US008668654B1

(12) United States Patent
Gerrans et al.

(10) Patent No.: US 8,668,654 B1
(45) Date of Patent: Mar. 11, 2014

(54) CYTOLOGICAL BRUSHING SYSTEM

(71) Applicants: Lawrence J. Gerrans, San Anselmo, CA (US); Erhan H. Gunday, Great Neck, NY (US)

(72) Inventors: Lawrence J. Gerrans, San Anselmo, CA (US); Erhan H. Gunday, Great Neck, NY (US)

(73) Assignee: Sanovas, Inc., Sausalito, CA (US)

( * ) Notice: Subject to any disclaimer, the term of this patent is extended or adjusted under 35 U.S.C. 154(b) by 0 days.

(21) Appl. No.: 13/800,623

(22) Filed: Mar. 13, 2013

(51) Int. Cl.
*A61B 5/00* (2006.01)

(52) U.S. Cl.
USPC .......................................... 600/562; 600/569

(58) Field of Classification Search
USPC ................... 600/562–564, 569–572
See application file for complete search history.

(56) References Cited

U.S. PATENT DOCUMENTS

| 4,324,262 | A | 4/1982 | Hall |
|---|---|---|---|
| 5,056,529 | A | 10/1991 | de Groot |
| 5,919,145 | A | 7/1999 | Sahatjian |
| 6,398,775 | B1 | 6/2002 | Perkins et al. |
| 6,527,761 | B1 | 3/2003 | Soltesz et al. |
| 7,670,282 | B2 | 3/2010 | Mathis |
| 7,775,968 | B2 | 8/2010 | Mathis |
| 8,226,601 | B2 | 7/2012 | Gunday et al. |
| 2009/0099414 | A1 | 4/2009 | Goto et al. |
| 2012/0226103 | A1 | 9/2012 | Gunday et al. |

*Primary Examiner* — Max Hindenburg
(74) *Attorney, Agent, or Firm* — St. Onge Steward Johnston & Reens LLC

(57) ABSTRACT

A system for gathering biological material in a biological cavity comprising a catheter having a first lumen, a balloon, and a second lumen in fluid communication with said balloon. The balloon has a textured outer surface for collecting biological material. At least one device for sampling a bodily tissue, such as a needle, optic or forceps, is disposed in the first lumen. A fluid source in fluid communication with the balloon supplies fluid to the second lumen to inflate the balloon such that the textured outer surface collects additional biological material. The system is particularly useful for collecting samples in the lungs or bronchial airways, such as at a bronchial junction.

28 Claims, 20 Drawing Sheets

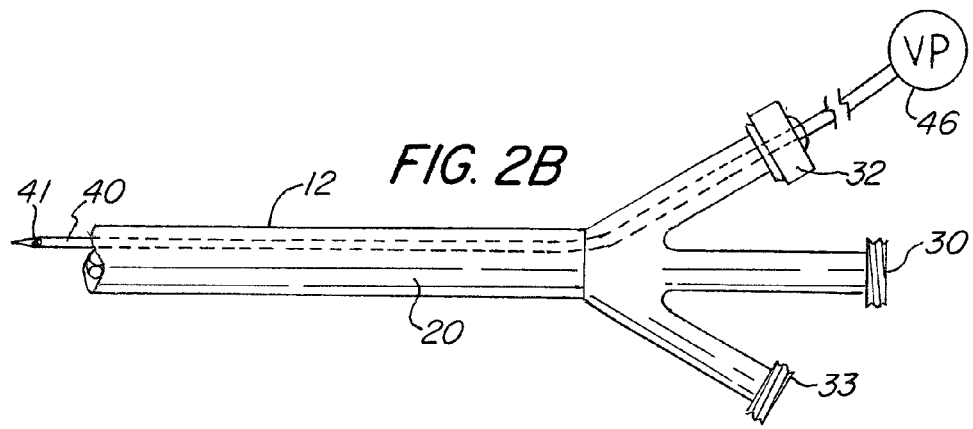
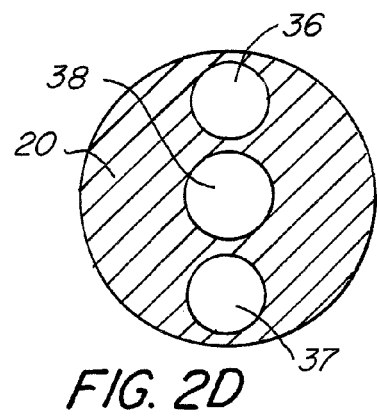
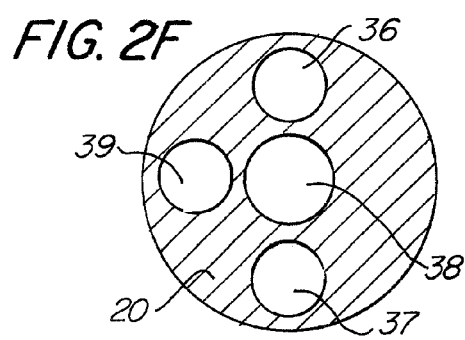
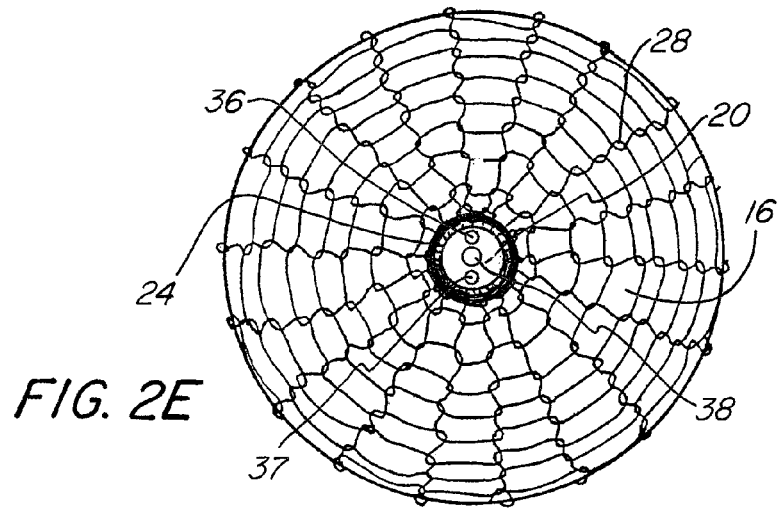

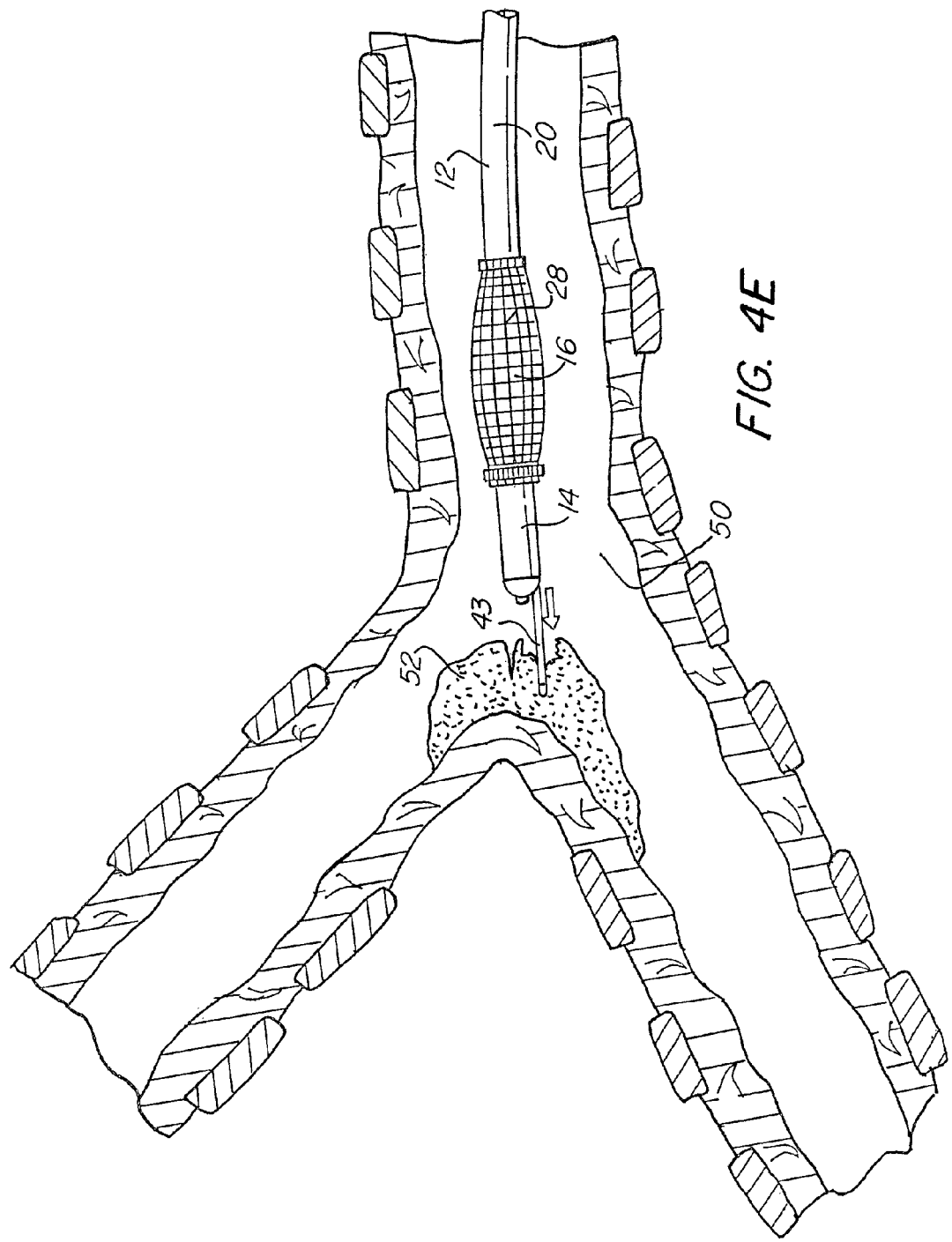

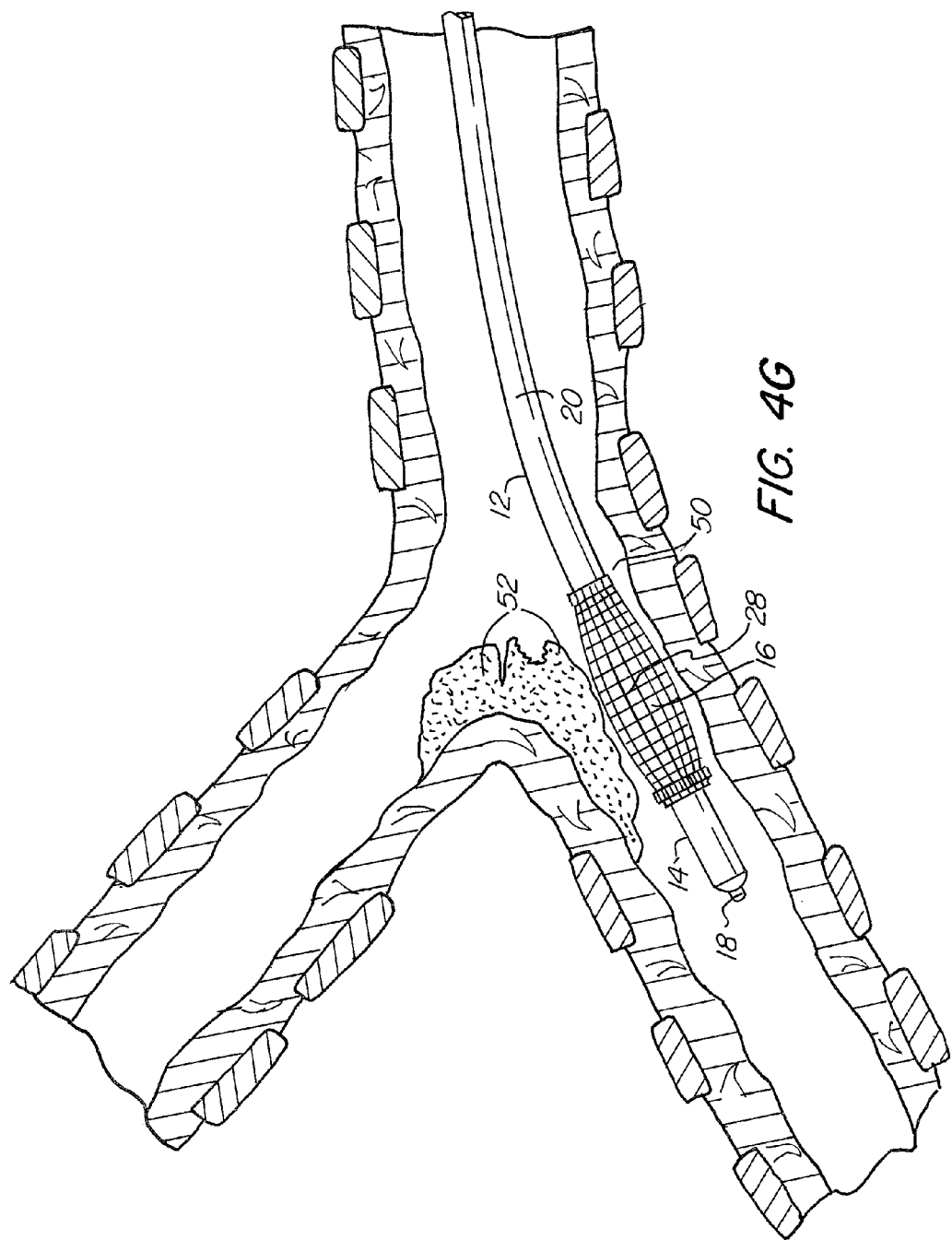

CYTOLOGICAL BRUSHING SYSTEM

FIELD OF THE INVENTION

The present invention relates to systems and methods for obtaining biological samples from bodily tissues and cavities. More specifically, the invention relates to a system and method for efficiently collecting biological samples from a plurality of disparate sites within a bodily cavity using a variety of tools delivered through a lumen of a balloon catheter to obtain specimens of biological material from and/or adjacent to the cavity and inflating the balloon of the catheter, which has a textured outer surface for collecting additional biological material.

BACKGROUND OF THE INVENTION

Samples of tissue and bodily fluids are frequently taken from patients for analysis to help in diagnosing disease or monitoring the progress of treatment. Samples may be obtained from a cytological brush, which obtains cells from a mucosal surface using bristles. Aspirates may be obtained from superficial or internal lesions by suction through a fine needle or forceps. Core samples may be obtained from sub mural, sub mucosal, smooth muscle and related tissues adjacent to these cavities. Diagnostic molecular images may be obtained from tissues using optical imaging techniques, such as confocal laser microscopy. Various instruments and methods have been employed to perform these procedures, which are generally well known in the art.

Often, the cytology brush is literally a brush containing bristles that is rubbed on the outer surface of tissues. The bristles are mounted on a wire and may be combined with a needle tip. Typical complications result from kinking of the brush wire, brush hardness and thickness of the bristles.

Needles and forceps are used to sever tissue from the body. For example, biopsies are taken with a needle device that penetrates the tissue and then severs a sample with a sharp cutting cannula. A biopsy forceps having a jaw-type cutter at its end is another example.

An instrument that is commonly used in various types of medical procedures is an inflatable balloon catheter, of which many different types exist, which are utilized to perform various necessary functions. For example, these inflatable balloons are often used to control or stop bleeding, to hold instruments in place, or to prevent or facilitate other flow or movement within the bodily cavity. For example, many urological catheters are held in place via a balloon that impacts the sidewalls of the urinary tract, many gynecological instruments are held in place via balloons that impact the sidewalls of the vaginal vault, endovascular balloons are often used to control bleeding, inflatable balloons are sometimes used to control the backflow of radio-opaque agents injected into the cystic duct to detect the presence of gall stones during general surgical cholecystectomy procedures, and, recently, balloon catheters have been employed to release sinus congestion.

One particular application of such catheters is lung cancer. Among all types of cancer, this has the lowest survival rate, as more than one third of all deaths due to cancer are caused by lung cancer. In the treatment and diagnosis of lung cancer, it is necessary to obtain various biological samples from the lung.

Several devices have been proposed to collect biological samples in internal cavities, and particularly, the lung. For example, U.S. Pat. No. 5,919,145 (Sahatjian) discloses a balloon catheter having a balloon with a porous, hydrogel polymer that swells when exposed to body fluids/tissues, and thus, collects bodily samples. The balloon can be expanded and contracted to create a suction force that pulls sample into the polymer. The goal is to avoid mechanically disturbing the vessel to avoid causing injury.

U.S. Pat. No. 6,398,775 (Perkins et al.) discloses a balloon catheter for isolating a target lung segment and collecting aspirates and/or delivering drug to the isolated segment. Similarly, U.S. Pat. No. 6,527,761 (Soltesz et al.) discloses a catheter for collecting aspirates. An anchor, which may be a balloon, is used to anchor the catheter for aspiration.

Further, U.S. Pat. Nos. 7,670,282 and 7,775,968 (Mathis) disclose a balloon catheter for delivery of a biopsy needle. The balloon is used to move the needle towards to the biopsy site. Alternatively, a cutter tool may be used to collect sample.

While the above described systems are useful for collecting samples within a patient's body, these systems still suffer from a number of disadvantages and drawbacks. One of the major problems with the prior art systems described above is that multiple types of samples cannot be collected at the same time or with the same catheter. Additionally, these known systems are typically constructed with expensive materials and require multiple working components, and therefore, have to be reused multiple times, which requires complex sterilization procedures.

A further deficiency of the prior art systems described above is that they are not capable of being positioned as optimally and precisely as may be desired. The known devices do not provide illumination and a direct visual feedback of the area ahead, behind, and around the device to optimize positioning and operation of the device.

In light of the prevalence and seriousness of pulmonary diseases, such as lung cancer, there is a need to obtain cell and tissue samples from the respiratory tract. In particular, there is a need to obtain biopsies, aspirates and cytological specimens in the target junctions of bronchial airways in an efficient and cost-effective manner.

What is desired, therefore, is an improved system and method for collecting biological samples at specific locations inside a patient's body that addresses the disadvantages and shortcomings of the prior art systems described above.

SUMMARY OF THE INVENTION

Accordingly, it is an object of the present invention to provide a cytological brushing system that can obtain multiple types of biological samples from a target site.

It is another object of the invention to provide a cytological brushing system that can safely and quickly obtain the biological samples with the introduction of a single catheter.

It is yet another object of the invention to provide a cytological brushing system that facilitates optimal and precise positioning of the devices collecting the sample.

In order to achieve at least the above-mentioned objects, the present invention provides a system for gathering biological material in a biological cavity comprising a catheter having a first lumen, a balloon, and a second lumen in fluid communication with the balloon. The balloon has a textured outer surface for collecting biological material. The system further comprises at least one device for sampling biological material movably disposed in the first lumen; and a fluid source in fluid communication with the balloon that supplies fluid to the second lumen to inflate the balloon such that the textured outer surface collects additional biological material. The system of the present invention can be made in a variety of sizes and have an outer diameter appropriate such that it can be deployed through a working channel of standard bronchoscopes.

In some embodiments, the at least one device for sampling biological material is a forceps. In other embodiments, the at least one device for sampling biological material is a needle. In certain embodiments, the at least one device is both a needle and a forceps. In some embodiments, the needle comprises a lumen fluidly connected to an opening at a distal end of the needle. In some embodiments, the system further includes a vacuum source for vacuuming material through the lumen of said needle.

In certain embodiments, the system further comprises at least one auxiliary lumen. In some embodiments, an imaging device is disposed in the second lumen or the auxiliary lumen.

In some cases, the fluid source comprises an electro-pneumatic pump. In some of these embodiments, the pump supplies gas.

In certain embodiments, the textured surface of the balloon is a mesh. In some of these embodiments, the mesh comprises elastane.

In some embodiments, the catheter includes an imaging device aperture, and further comprises a fiber optic bundle disposed in the catheter and movable through the aperture for viewing the biological cavity.

In certain embodiments, the system includes an oxygen sensing probe for determining the partial pressure of oxygen in the biological material.

In certain embodiments, the catheter includes a molecular imaging device aperture, and the system further includes a fiber optic bundle disposed in the catheter and movable through the aperture for acquiring diagnostic images from the biological cavity. In other embodiments, this device for acquiring the diagnostic images is a laser fiber. In certain embodiments, the system includes a fiber optic imaging device, a laser fiber, and a needle.

In some embodiments, the needle comprises a lumen fluidly connected to an opening at a distal end of the needle. In some embodiments, the system further includes a vacuum source for vacuuming material through the lumen of said needle.

In some cases, the catheter comprises an imaging marker. In certain embodiments, the balloon has first and second ends further comprising at least one imaging marker mounted adjacent at least one of the first end and second end of the balloon.

A method for gathering biological samples in a biological cavity is also provided comprising the steps of inserting into a biological cavity a catheter having a first lumen, a balloon, and a second lumen in fluid communication with said balloon. The balloon has a textured outer surface for collecting biological material. At least one device for sampling biological material is inserted into and through the first lumen of the catheter and collects biological material, and fluid is supplied through the second lumen to inflate the balloon such that the textured outer surface comes into contact with and collect additional biological material. In some embodiments, the biological cavity is in a bronchial airway or lung.

In some embodiments, the at least one device is a forceps, and the step of collecting biological material comprises severing a portion of a biological target. In some embodiments, the device is a needle, and the step of collecting biological material comprises puncturing the biological target with the needle. In certain embodiments, the device is extended through the distal tip of the catheter.

In some cases, the method further comprises the step of extending an imaging device through an additional lumen of the catheter and through the distal tip.

In certain embodiments, the method includes the steps of inflating the balloon to stabilize the catheter within the biological cavity, and inserting an optical fiber through an additional lumen of the catheter to obtain a diagnostic image of the biological material.

In some cases, the method includes the step of inserting an oxygen sensing probe through an additional lumen of the catheter to determine the partial pressure of oxygen in the biological material.

In some embodiments, the method further includes sweeping the inflated balloon along the bronchial airway.

In certain cases, the method further comprises the step of evacuating biological samples through an additional lumen of the catheter using a vacuum source.

Other objects of the invention and its particular features and advantages will become more apparent from consideration of the following drawings and accompanying detailed description.

BRIEF DESCRIPTION OF THE DRAWINGS

FIG. 2B is an elevation view of the proximal portion of a catheter system of the present invention.

FIG. 2D is a cross sectional view of the catheter of FIG. 1 along the line 2-2 with the balloon in the deflated state.

FIG. 2E is a cross-sectional view of the balloon of FIG. 1 along line 2-2 with the balloon in an inflated state.

FIG. 2F is a cross sectional view of the catheter of FIG. 1 along the line 3-3.

FIGS. 4A-4I are side elevation views of a balloon catheter system of the present invention deployed in a bronchus of the lung.

DETAILED DESCRIPTION OF THE INVENTION

Figure 1:
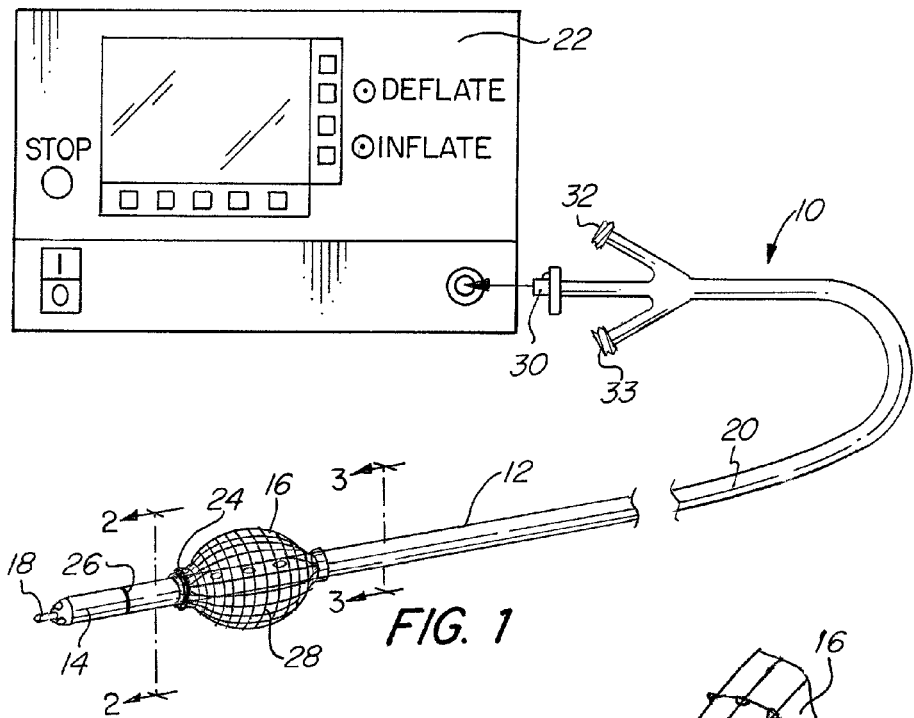
FIG. 1 is a schematic view of a system for gathering biological material in a biological cavity in accordance with the present invention.

The basic components of one embodiment of a cytology brush balloon catheter system in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system for gathering biological material in a biological cavity of the present invention may be used to collect samples in specific locations within a patient's body. For example, the present invention can be used to collect samples within and adjacent to bodily cavities, such as tubular structures, lumens, pleural cavities, airways, vessels, organs, bones and joints. The system of the present invention can be made in a variety of sizes and have an outer diameter appropriate such that it can be deployed through a working channel of standard bronchoscopes.

The system for gathering biological material in a biological cavity can be introduced into a patient's bodily cavity independently, or may be deployed via, for example, a guiding catheter, a working channel of a rigid or flexible endoscope, or any other suitable guiding device. In one advantageous embodiment, the system is used with a steerable catheter system described in U.S. Patent Application Publication No. 2012/0226103 by Gunday et al., the disclosure of which is also incorporated by reference herein in its entirety.

FIG. 1 illustrates one exemplary embodiment of the system for gathering biological material in a bodily cavity. The system (10) includes a fluid source (22) from which a physician or assistant can control the system (as well as a remote control unit), which is further described below. A balloon catheter (12) is connected to the pump (22), to which the pump (22) supplies a fluid, such as a gas, liquid, or mixture thereof. The balloon catheter (12) includes a catheter (20) made of any commercially available material that is flexible enough to allow the shaft to be safely inserted through the available opening of a bodily cavity. A bendable section (14) at the distal end of the catheter (12) serves as a safety tip to ensure safe and non-traumatic insertion of the shaft into bodily cavities. As a result, when the catheter (12) is inserted through the available opening of a bodily cavity, it will bend instead of puncturing the walls of the cavity.

In some embodiments, the catheter body (20) includes a coating made of suitably smooth material to facilitate the movement of the shaft through the bodily cavities. In some advantageous embodiments, the catheter (20) consists of a coil wire made of any suitable material, such as stainless steel, and a coating made of suitable materials, such as polyethylene, polyurethane, Pebax® and the like. A braided sheath may also be used instead of the coil wire. In some advantageous embodiments, the coil wire or the braided sheath may be made with a memory shape material, such as nitinol.

In further advantageous embodiments, the catheter (20) includes a combination of braided sheath and coil wire materials to provide for optimal flexibility and maneuverability of the shaft. For example, the distal portion (14) of the catheter (20) may be made with coiled wire material and the rest of the shaft may be made with the braided sheath material.

The coil wire or braid can be molded over during the shaft extrusion process and can run the entire length of the catheter (20). Alternatively, the catheter (20) may be molded or extruded in a first step and the coil wire may be disposed within a lumen of the catheter body (20). Such design improves torque, maneuverability, and kick resistance of the catheter (20), and also prevents reduction of the catheter's inner diameter.

In some advantageous embodiments, such as shown in FIG. 1, the balloon catheter (12) further includes imaging markers (26) positioned at the distal end (14) of the catheter (20) or at any other location along the catheter body (20) to facilitate external imaging thereof, and to thereby allow for better visualization during insertion and positioning of the system (10) in bodily cavities.

The balloon (16) is positioned at or near the tip of the distal end (14). The inflatable balloon (16) may be made of latex, Yulex, polyurethane, silicon, chronoprene, chronoflex, chronosil, nylon or other suitable material, and may come in a variety of sizes and diameters, depending on a particular application. In certain advantageous embodiments, a compliant balloon is employed. In further advantageous embodiments, the inflatable balloon (16) comprises a plurality of balloons/bladders, which may be controlled, inflated and deflated independently of each other.

The inflatable balloon (16) has an outer wall with a textured surface (28), such as a woven mesh. When inflated, textured surface (28) can brush, rub or abrade against the lumen wall, tumors or cysts, or other biological material to be sampled to collect cytological specimens. Additionally, the textured surface (28) assists in precisely positioning the medical instrument by ensuring that it does not slip, and also ensures more uniform expansion of the balloon (16) upon inflation.

The catheter body (20) has at least one inner lumen for supplying fluid to the balloon (16) to inflate it. As shown in FIG. 1, the inflation lumen is connected to a fluid source (22), such as a syringe or a pump, connected to a proximal end of the balloon catheter (12) via a suitable connection mechanism (30). The inflation lumen of the catheter (20) is in fluid communication with the interior of the inflatable balloon (16) via a plurality of openings in the shaft wall positioned inside the balloon (16), as illustrated in FIG. 1. Though pictured with a pump, any suitable fluid source may be used in accordance with the present invention.

In one advantageous embodiment, the fluid source (22) is an electro-pneumatic pump having controls on the front thereof, from which a physician or assistant can control the system (as well as a remote control unit), such as that disclosed in U.S. Pat. No. 8,226,601 to Gunday et al., the disclosure of which is hereby incorporated by reference herein in its entirety. The pump (22) supplies a fluid, such as a gas, liquid, or mixture thereof, to the catheter (12) via an inflation port (30) to inflate the balloon (16). In certain advantageous embodiments the pump (22) also supplies a therapeutic and/or diagnostic agent, drug, gel, nanoparticle or mixture thereof, to the catheter (12) via the inflation port (30). The pump (22) also includes a variety of capabilities for balloon identification, proper inflation/deflation of the balloon, and feedback measurements, many details of which are described in Gunday et al. In certain advantageous embodiments, the pump (22) further includes a vacuum source to evacuate fluid from the balloon (16). In other embodiments, a handheld pump or a syringe is used as a fluid source.

In some embodiments, the system (10) includes a data device, such as optical, RFID, flash memory, etc. This way, the pump (22) is able to identify the type of system that is connected to it and read the characterization data of the balloon, e.g. maxim pressure, volume, dimensions, etc., and then adjust its control accordingly based on user input.

The pump (22) may further include a processor to control the supply of fluid to the inflatable balloon (16) based on at least one predetermined parameter. In some embodiments, such predetermined parameters may be manually entered by the user. Alternatively, the control of the fluid is based on default parameters selected by the pump (22), which are based on the characteristics of the particular balloon and/or measurements of dimensions of a particular bodily cavity made by the pump. Furthermore, the pump may control and regulate the pressure by monitoring and taking into account one or more vital signs and physiological parameters of the patient, such as body temperature, heart rate, blood pressure, and respiratory rate.

Figure 2A:
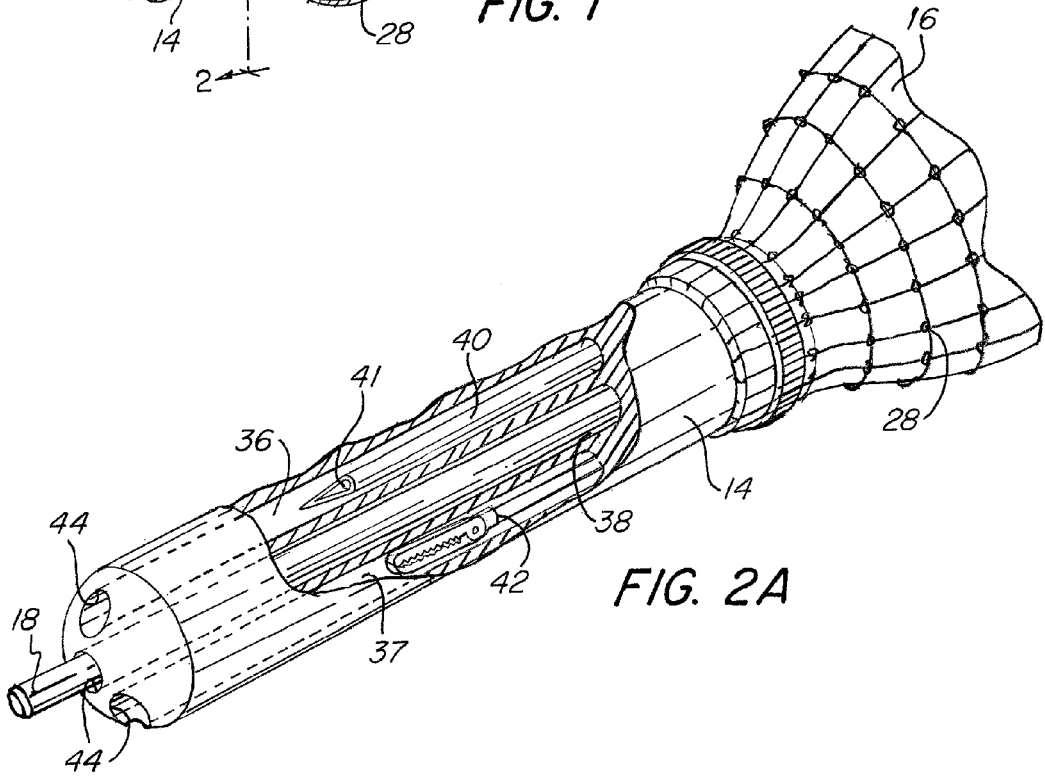
FIG. 2A is a perspective, partially exposed view of the distal tip of the catheter used in the system of FIG. 1.

It should be noted that the catheter (20) has one or more lumens for various purposes, for example, for introduction of an imaging device and/or an illumination device (18) to assist in proper positioning of the catheter (12), together with a desired medical device, relative to a target site. In one advantageous embodiment, as shown in FIG. 2A, the distal end of the catheter (14) has one or more openings (44), and the imaging and/or illumination device (18) is extended out of a lumen through the opening (44) for viewing, sampling and/or modifying the surrounding tissue. In another advantageous embodiment, the distal end of the catheter (14) includes a transparent membrane, such that the imaging/illumination device (18) positioned in the lumen is capable of viewing/modifying the tissue in front of the balloon (16) through the transparent membrane. In yet another advantageous embodiment, an outer wall of the inflatable balloon (16) is transparent, and an imaging device, an illumination device, and/or energy source disposed in the lumen extends out through one of the openings inside the balloon for viewing and/or delivering energy to the surrounding tissue. A distal tip of the imaging/illumination device (18) may be rotatable such that a complete 360 degree view of the surrounding tissue may be obtained.

As shown in FIG. 2A, the catheter body (12) includes three working lumens (36, 37, 38) that extend the entire length of the body and pass to proximal connectors (32, 34). The lumens (36, 37, 38) can be used for introducing the imaging device and/or an illumination device (18) or for inserting and/or removing materials which are introduced into or withdrawn from a bodily cavity via a cell or tissue collection device (40, 42). For example, when a transbroncheal biopsy is conducted, a long thin cannula needle (40) may be delivered to the lung through a lumen (36). The needle (40) comprises an elongated shaft with at least one opening at a distal end thereof. The opening is fluidly connected with a needle lumen (41) for evacuating fluids or biological samples from the bodily cavity or, in some embodiments may be use for delivering a desired therapeutic and/or diagnostic agent to tissue. The elongated shaft is made with any suitable biocompatible material, such as stainless steel or plastic. As another example, if tissue of a lesion is to be sampled, biopsy forceps (42) are advanced through a lumen (37) to the vicinity thereof. Biopsy forceps (42) may be of any kind commonly used in the art.

Figure 2C:
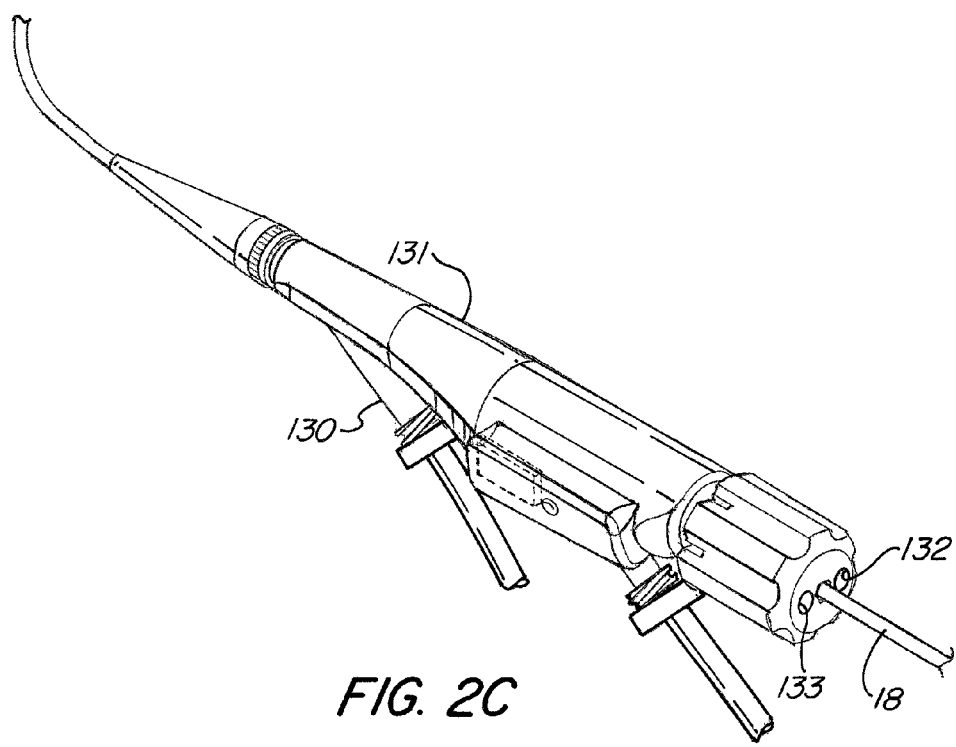
FIG. 2C is an elevation view of the proximal portion of a catheter system of the present invention.

A proximal end of the catheter (12) is illustrated in FIG. 2B. The proximal end includes an inflation port (30) for connection of the catheter (12) to the fluid source (22), through which the balloon (16) is inflated. The inflation port (30) is provided with any suitable connector, such as a luer connector, for connection to the fluid source (22). The proximal end further includes one or more medical device insertion ports (32, 33), through which a desired medical instrument or device, such as a needle member (40), is inserted into the catheter body (20). It is noted that additional ports may be provided at the proximal end for insertion of additional devices. For example, a separate imaging port may be provided for insertion of the imaging device into catheter (20). Alternatively, the imaging device may be inserted through a medical device insertion port (32). Similarly, as illustrated in FIG. 2C, the needle member (40) and forceps (42) may be inserted into rear ports (132, 133) of a catheter hub (131), which receives balloon inflation air from a handheld pump via inflation port (130).

As shown in FIG. 2B, in some embodiments, the cell or tissue collection device, in this case needle (40), may be fluidly coupled to a vacuum pump (46) for aspirating material through a lumen (41) in the needle (40).

In some embodiments, the needle (40) has more than one inner lumen (41). For example, the needle (40) may have one lumen (41) for aspirating material and one or more delivery lumens for individual or simultaneous delivery of one or more different therapeutic or diagnostic agents. In other embodiments, two needle members may be used to collect samples or deliver agents. Once two needle members and/or one needle member with a dual inner lumen is inserted into a target tissue, different therapeutic and/or diagnostic agents are injected out of the distal tip of each needle and/or lumen opening, causing the agents to mix within the target tissue.

In some advantageous embodiments, the needle member (40) may also include at least one conductive probe, e.g. an electrode or an optical device, such as an optical fiber, capable of conducting infra red (IR) light, near infra red (NIR) light, ultra violet (UV) light and/or ultrasound waves, to assist in diagnosis and/or treatment of specific medical conditions. In additional advantageous embodiments, an energy emitting device, such as a radiation emitting probe may be used in addition to, or in place of, the needle member (40).

In further advantageous embodiments, needle member (40) can supply additional media to tissue, e.g. medical grade oxygen. For example, tumor tissues are known to be hypoxic (having low concentrations of oxygen), and do not respond well to radiation treatment. Therefore, measuring the oxygen pressure and delivering oxygen to increase the oxygen concentration, coupled with a synchronized triggering of the radiation treatment, is important in treatment of the tumor tissues. For example, partial pressure of oxygen in a target tumor tissue is measured first by a sensor provided on the needle member, then a biopsy tissue specimen is obtained via the needle member or other biopsy device, such as forceps (42). Next, an oxygenating agent is delivered to tumor tissue, if necessary together with a chemotherapeutic drug and/or any other therapeutic agent, via the needle member. Then, a radiation probe is inserted to locally deliver targeted radiation to the tumor tissue.

In an advantageous embodiment, the needle member (40) further includes at least one sensor for measuring various characteristics of bodily tissue to facilitate precise and efficient sampling or delivery of a drug or diagnostic agent. For example, it may be desirable to measure oxygen concentration of tissue, such as cancerous tissue. Any type of suitable sensor can be used in accordance with the present invention. The sensors are positioned at or in proximity of the distal tip or any other suitable location along the needle.

In some advantageous embodiments, the proximal end of the balloon catheter (12) may include calibrated markings to gauge the extent of insertion of the catheter (12) into a bodily cavity.

The proximal end may also be connected to a control device, such as a hand piece, for actuation of the system (10) by a physician. In some embodiments, the control device is used to inflate and deflate the balloon (16) provided at the distal end of the catheter (14). In these embodiments, the fluid source (22) may be connected directly to the control device via any type of suitable connector. The control device may also be used to move the balloon catheter (12) distally or proximally to facilitate more precise positioning of the balloon (16) relative to the target site.

Figure 3A:
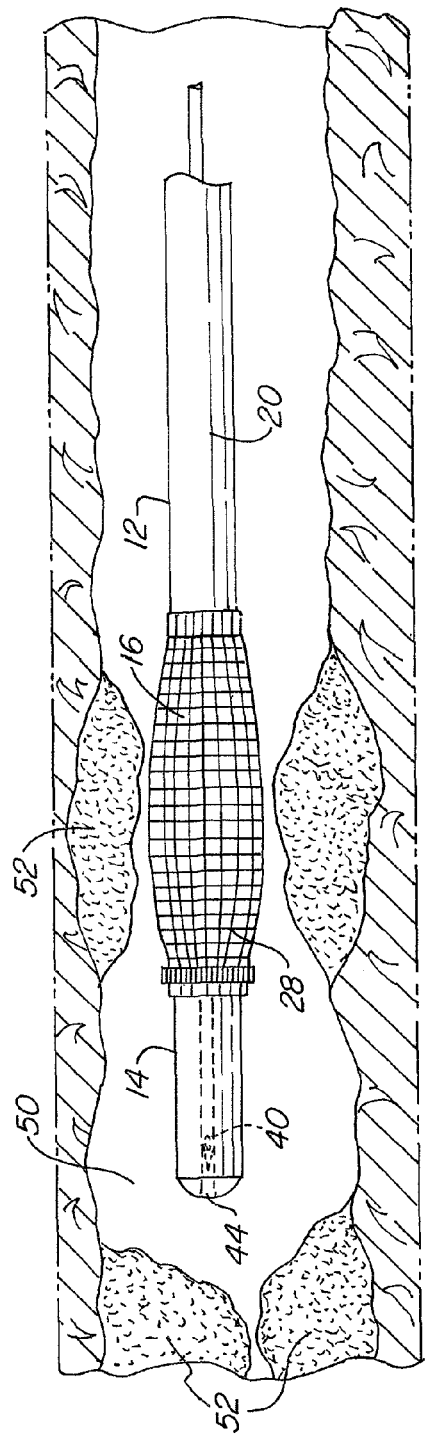
FIGS. 3A-3E are side elevation views of a balloon catheter system of the present invention deployed in a bodily cavity.
Figure 3B:
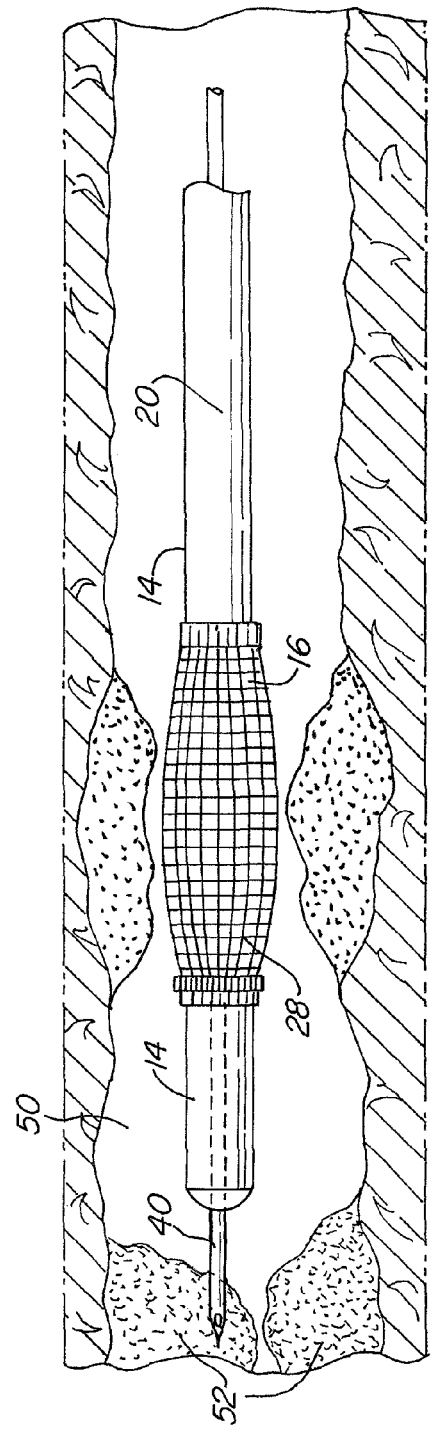

In additional embodiments, a control device may also be used to actuate the medical device, e.g. the needle member (40) or forceps (42) disposed in the catheter (20) from an inactivated position, as shown in FIG. 3A, to its activated position shown in FIG. 3B, and vice versa. The medical device may be inserted directly into the control device and may be actuated manually or via any suitable pneumatic mechanism. The medical device may also be rotated manually or via the control device to better position the device relative to the tissue site.

Turning now to FIGS. 2D-2E, FIG. 2D shows a cross-section of the catheter (12) at the distal end (14) along line 2-2 of FIG. 1 with the balloon (16) deflated. In certain embodiments, a working lumen (38) of the catheter (20) extends through the bendable section of the catheter tip (14) and is open at the distal end. An imaging device and/or illumination device may be employed through working lumen (38). In some embodiments, a fiber optic image bundle (18) is introduced through the lumen (38) center via a port (32, 132) provided at the proximal end to image the surrounding area. The fiber optic image bundle (18) can be made of an incoherent fiber bundle for illumination and a coherent imaging fiber bundle at the core, and a lens. The bundle (18) may incorporate various types of object lenses at the distal tip for different fields of view (i.e. 50°, 130°, etc.) and various depth of field. Two separate bundles, one for illumination and the other for imaging, can also be used. At the distal end of the fiber optic bundle (18), the imaging coherent fibers are separated from illumination fibers and interfaced to an image sensor, such as a CMOS or CCD, through appropriate optics. Similarly, the illumination fibers are interfaced to a light source. It should be noted, however, that other sources of illumination, such as light emitting diodes, may also be employed. It should also be noted that the image sensor can be located at the tip of the imaging catheter assembly, eliminating the need for a coherent imaging fiber bundle, thus increasing the image quality and reducing cost.

The imaging and/or illumination device (18) provides the physician or user with illuminated light, non-thermal illuminated light, and direct visual feedback of the surrounding area. In some advantageous embodiments, the imaging/illumination device (18) is extended through an aperture to illuminate and provide imaging of the target tissue site during the procedure and to facilitate positioning of the medical instrument, such as the needle (40) or forceps (42). The distal end of the imaging device (18) preferably has the ability to be actuated rotationally, thereby allowing for 360° visualization of the treatment area.

In certain applications, such as bronchoscopy, a working lumen (38) also serves as a passageway that allows the air to move freely in both directions from each end of the catheter (20) when the balloon (16) is inflated. Additionally, a working lumen (38) can be used as a means for accurately positioning the balloon catheter (12), as it can be used as a conduit for a guide wire when inserting the deflated balloon catheter (12) into the bodily cavity.

One or more auxiliary working lumens (36, 37) of the catheter (20) are used to introduce various cell or tissue retrieving instruments, such as the needle (40) or the forceps (42) previously mentioned. The auxiliary lumens (36, 37) also extend through the bendable section of the catheter tip (14) and are open at the distal end. As mentioned, the catheter also contains one or more inflation lumens (not pictured), which are blocked at the distal end of the balloon (16) so that air intended for inflation and deflation will not bypass balloon (16) and escape through the distal tip (14).

FIG. 2E shows a cross-section of the balloon of FIG. 1 along line 2-2 with the balloon (16) in an inflated state. The balloon is covered with a textured surface (28), which may, for example, comprise a fiber mesh affixed to the surface of the balloon (16). The textured surface (28) may be made by a woven mesh disposed on the outer surface of the balloon. The mesh may be made of elastane, latex, polyurethane, composite springs, metallic fibers, elastic, steel fibers, cotton yarn, or other appropriate material, or a composite or coating thereof. A mesh sleeve may be disposed on the outer surface of the balloon (16) by using any suitable manufacturing method. Alternatively, a mesh sleeve may be knitted or woven from thread directly onto the balloon (16). In other advantageous embodiments, dimensional surface structures, such as bumps or inflatable sinuses, that are encapsulated in the surface substrate of the balloon (16) may be used to produce the surface protrusions forming the textured surface (28).

The balloon (16) comes in a variety of sizes and diameters, which can be selected to suit the particular application for which the device is being used. Typically, such balloons will have lengths of 5, 10, 15, 20, 30 or 50 mm and diameters of 2.5, 5, 10, 15, 20, 30 or 50 mm. This variety of available balloon sizes allows the balloon catheter (12) to be used in bodily cavities of various diameters and dimensions, such as large and small bronchial branches, sinuses, and vessels, having different types of tumors and tissues to be treated. The fluid source (22) supplies the air at a pressure of approximately 2 atmospheres in order to be able to inflate such balloons to full size, ranging from 2.5 mml to 50 mml.

In certain advantageous embodiments, the balloon (16) includes imaging markers (24), such as radio opaque rings, located at or near the ends thereof. Such markers can be selected and appropriately positioned in order to reflect the relevant waves of various imaging modalities (e.g., x-ray) in order to allow the use of such modalities to assist with the precise positioning of the balloon (16).

FIG. 2F shows a cross section of the catheter (20) along line 3-3. Here, the catheter (20) includes an inner lumen (39), which is in fluid communication with the catheter openings in the balloon (16), through which the fluid source (22) supplies fluid to inflate the balloon (16).

A method for gathering biological material in a biological cavity in accordance with the present invention is illustrated in FIGS. 3A-3E. As shown in FIG. 3A, a balloon catheter (12) is inserted into a bodily cavity (50) with a needle (40) disposed therein and the balloon in a deflated state. In its inactivated position, the needle member (40) is extended to the distal tip (14) of the catheter (12) but does not extend out of opening (44). This way, the sharp tip of the needle member (40) remains completely housed within the catheter (10) thereby preventing possible injury to the patient during the insertion of the system (10) into the patient's body. Alternatively, the catheter (12) is first inserted into a bodily cavity (50) and the needle (40) is then inserted into the catheter (12).

Once the system (10) is inserted and positioned so that the tip (14) of the catheter is within the target bodily cavity (50) and next to the target site, the needle member (40) is moved into an activated position, as illustrated in FIG. 3B. Specifically, the needle member (40) is moved in a distal direction until it emerges from an opening in the distal tip (14) and contacts and penetrates the target bodily tissue (52).

Figure 3C:
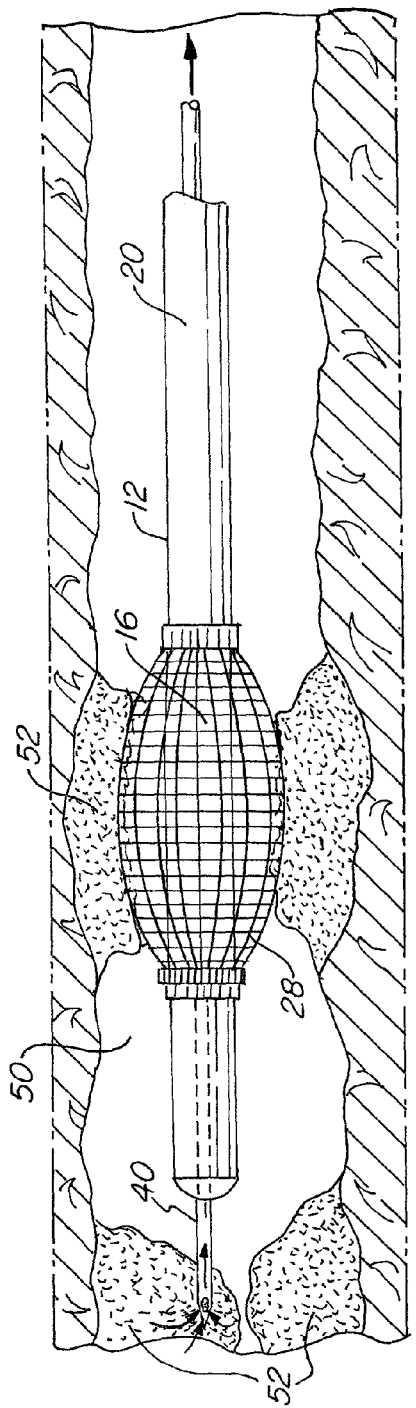
Figure 3D:
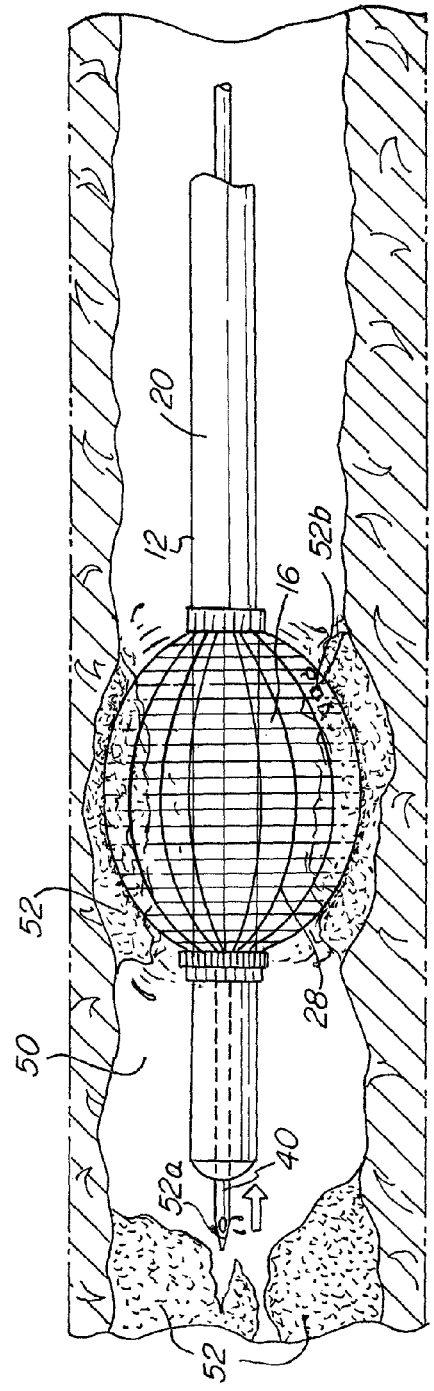

Next, as shown in FIG. 3C, a biopsy/aspirate is collected by the needle (40) and fluid is supplied to the inflation lumen within catheter (20) from the fluid source (22) to inflate the balloon (16). As shown in FIG. 3D, as the balloon (16) inflates, the textured surface (28) abrades the wall of the cavity and/or any tissue or tumor thereon (52), and collects a cytological sample (52E). At this point, the catheter (20) may be rotated by manual means or via the control device to better position the device relative to the tissue site and allow the textured surface (28) of balloon (16) to brush to the tissue and/or cavity wall to collect a cytological sample (52E). Likewise, the catheter may be moved back and forth along the bodily cavity so that the textured surface (20) brushes the tissue and collects the biological material. The needle is retracted from the tissue mass with the biopsy or aspirate (52D) therein.

Figure 3E:
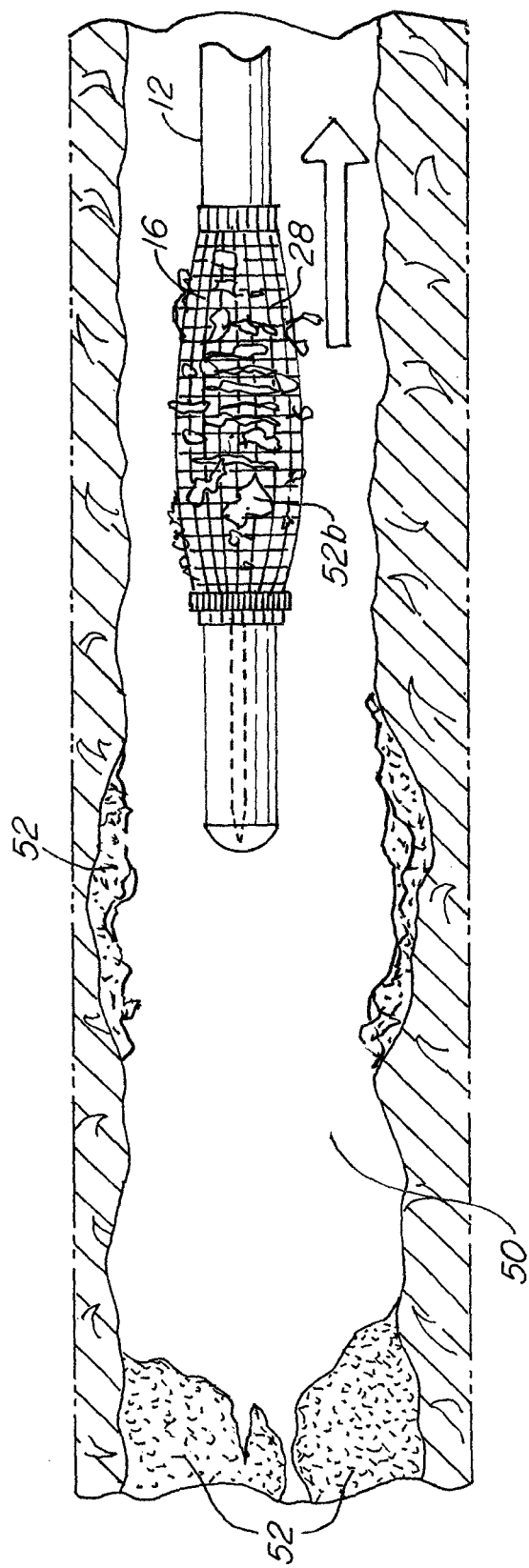

After the desired procedure is carried out completely, the balloon (16) is deflated, and the needle member (40) is moved proximally into an inactivated position shown in FIG. 3E, wherein the distal tip of the needle is completely enclosed by the catheter body (20). Then, the system is safely withdrawn from the patient's body.

In some advantageous embodiments, such as shown in FIGS. 4A-4G, the balloon catheter (12) of the system (10) is inserted into a bodily cavity, such as a bronchial junction, with an imaging means (18) disposed therein and the balloon (16) in the deflated state. As show in FIG. 4A, the imaging means (18) is used to position the catheter (12) within the target cavity (50) and to locate target bodily tissue (52).

Figure 4A:
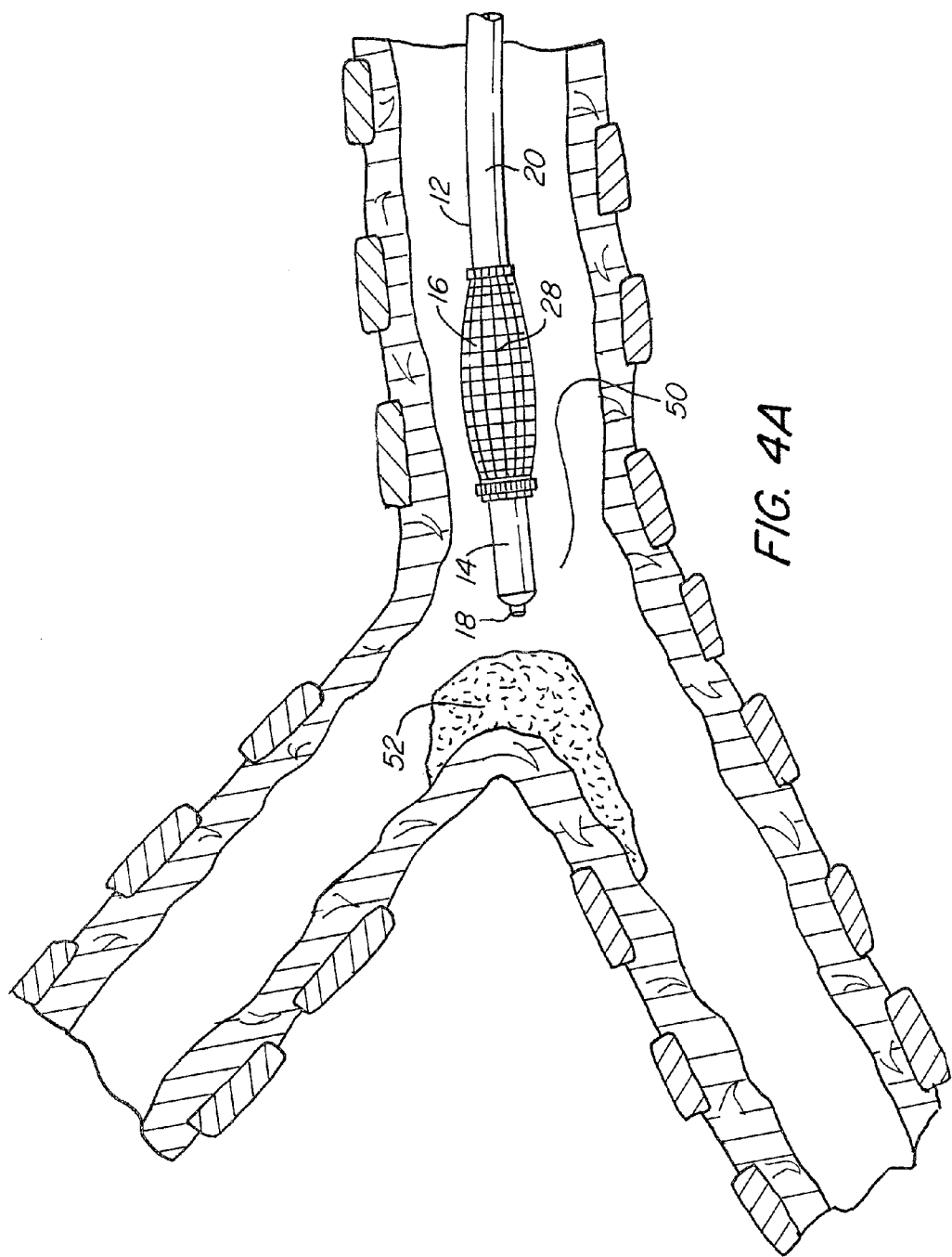
Figure 4B:
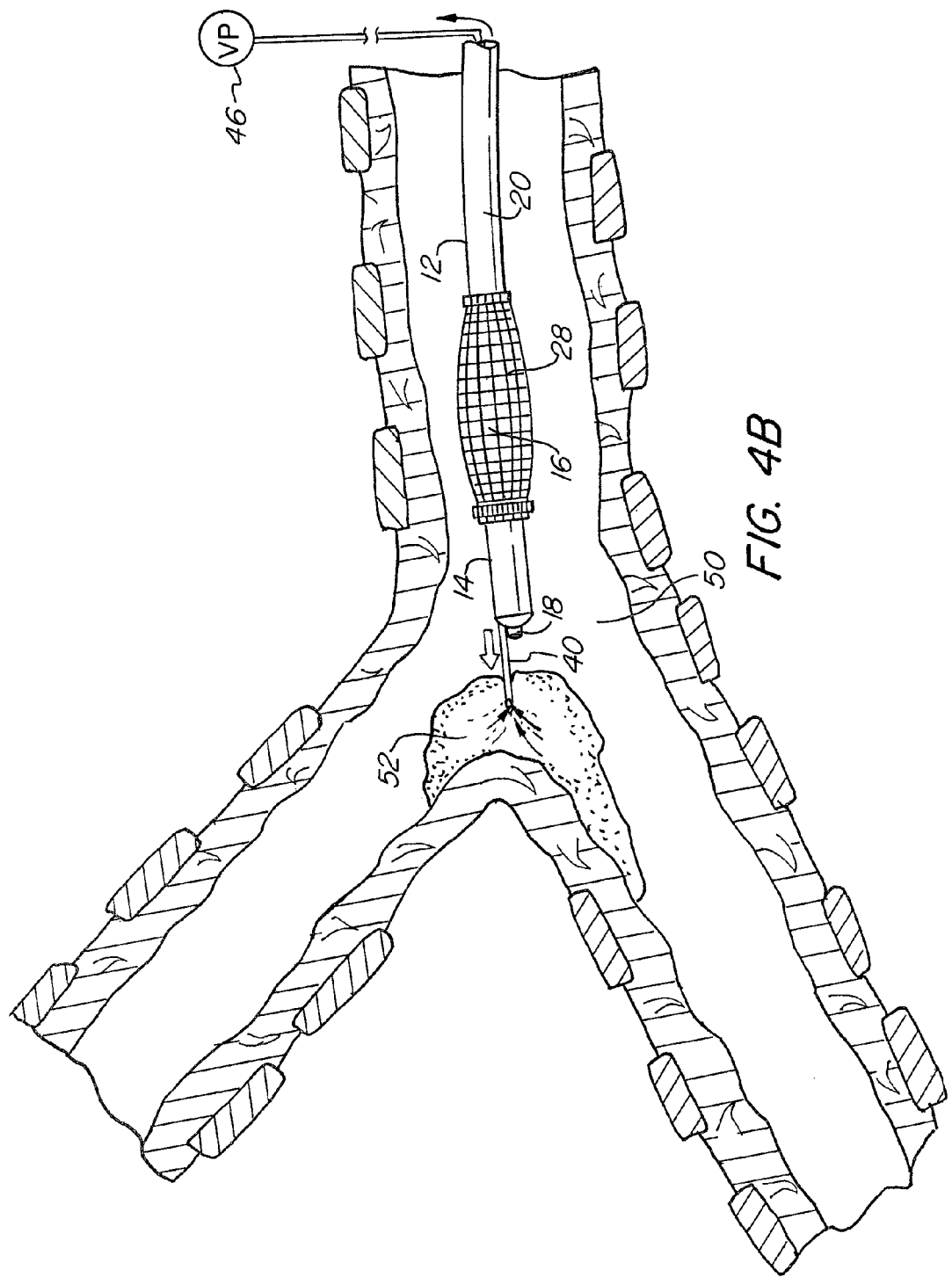

Once the catheter (12) is inserted and positioned within the target bodily cavity (50) near tissue site (52), a tissue collection device, such as needle member (40), is moved into an activated position, as illustrated in FIG. 4B. Specifically, the needle member (40) is moved in a distal direction until it emerges from distal tip (14) and contacts and penetrates the target tissue (52). An aspirate (52a) is collected by assistance of vacuum pump (46), which creates negative pressure to aid in removal of the sample from the cavity and into a lumen of needle (40).

Figure 4C:
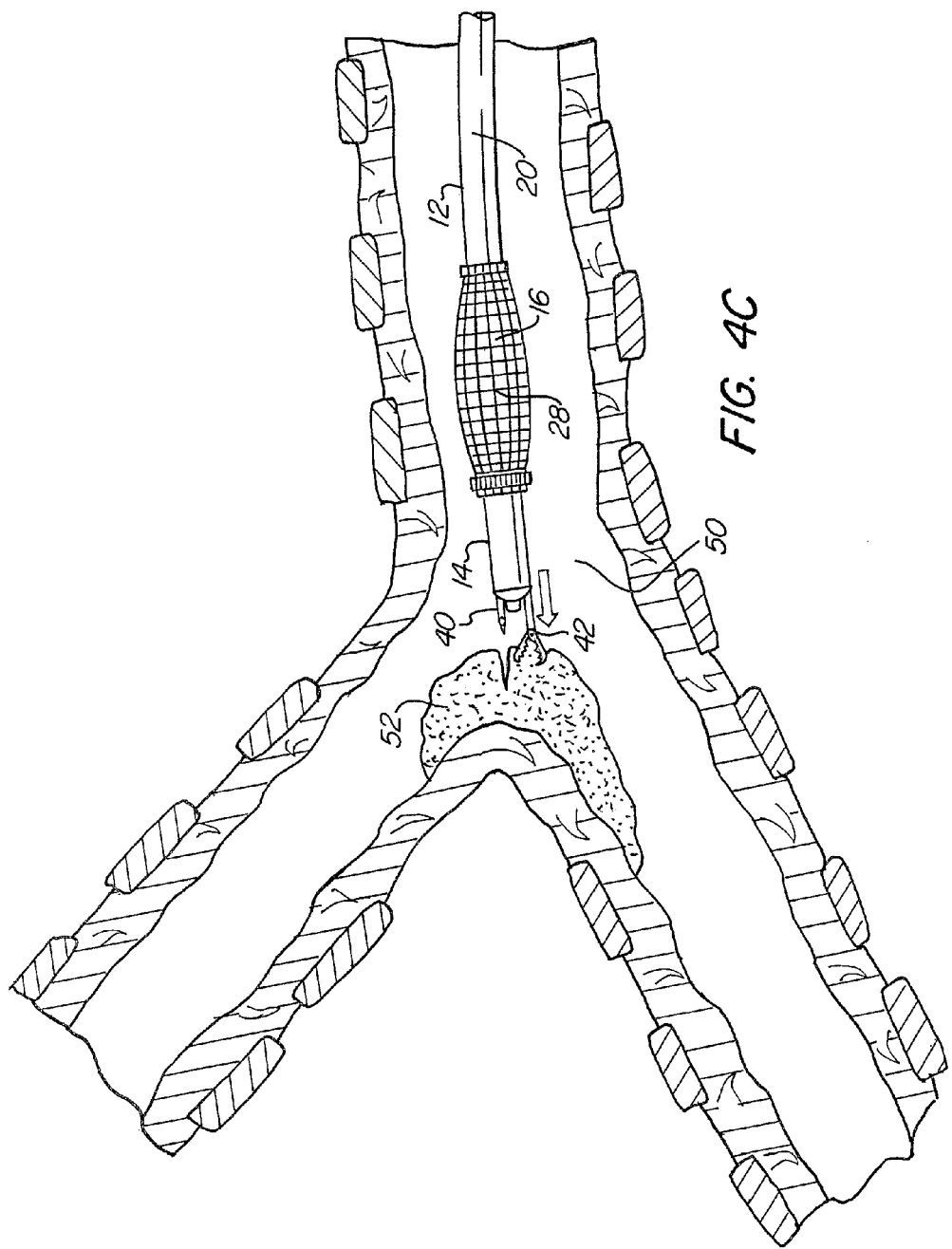
Figure 4D:
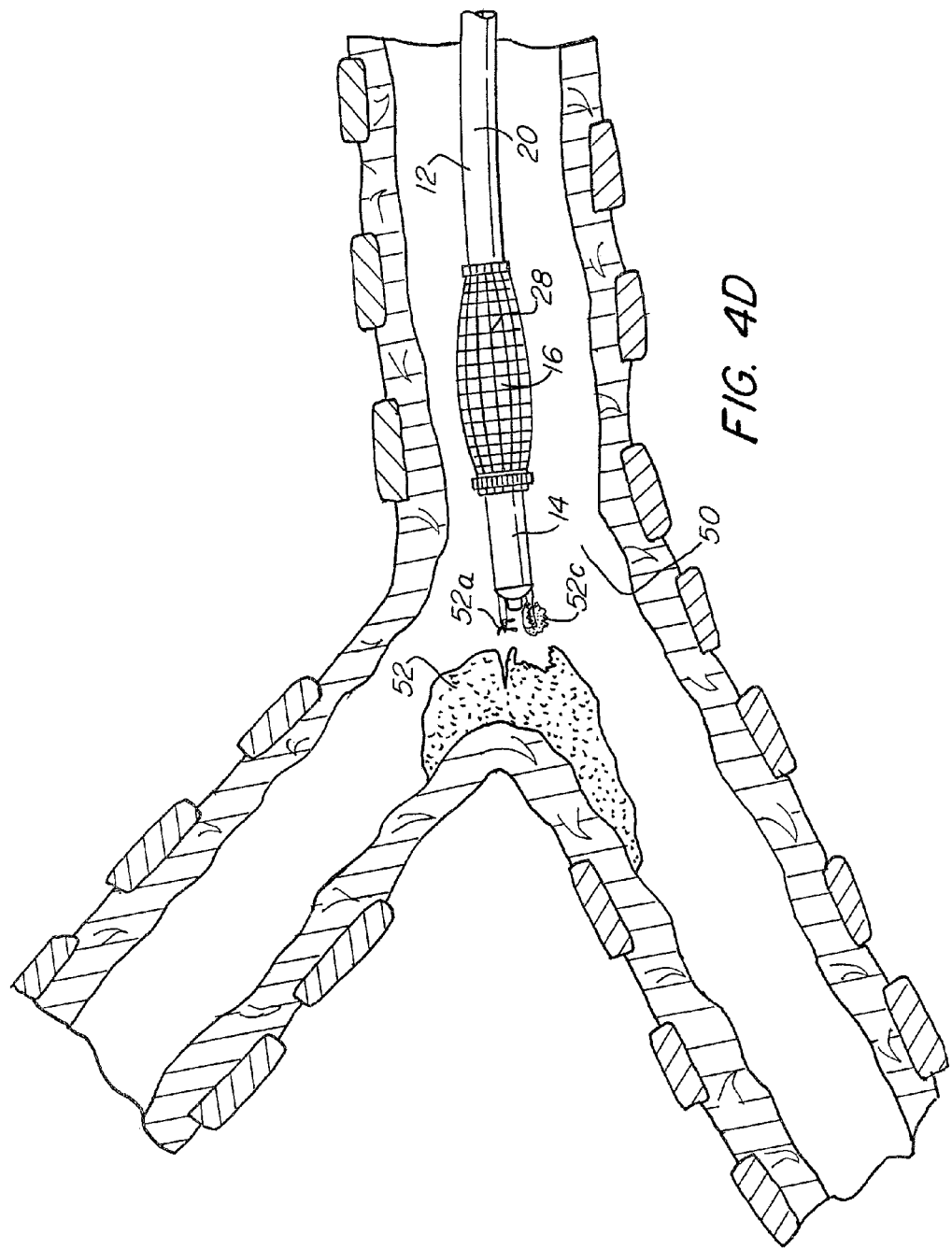

Next, as shown in FIGS. 4C-D, the forceps (42) is moved in a distal direction until it emerges from distal tip (14) and contacts the target tissue to collect a biopsy (52c). Alternatively, forceps (42) may first be deployed out the tip of the catheter (14) to collect a biopsy followed by needle (40). Following or at the same time, fluid is supplied to the inflation lumen within catheter (20) from the fluid source (22) to inflate the balloon (16).

Figure 4F:
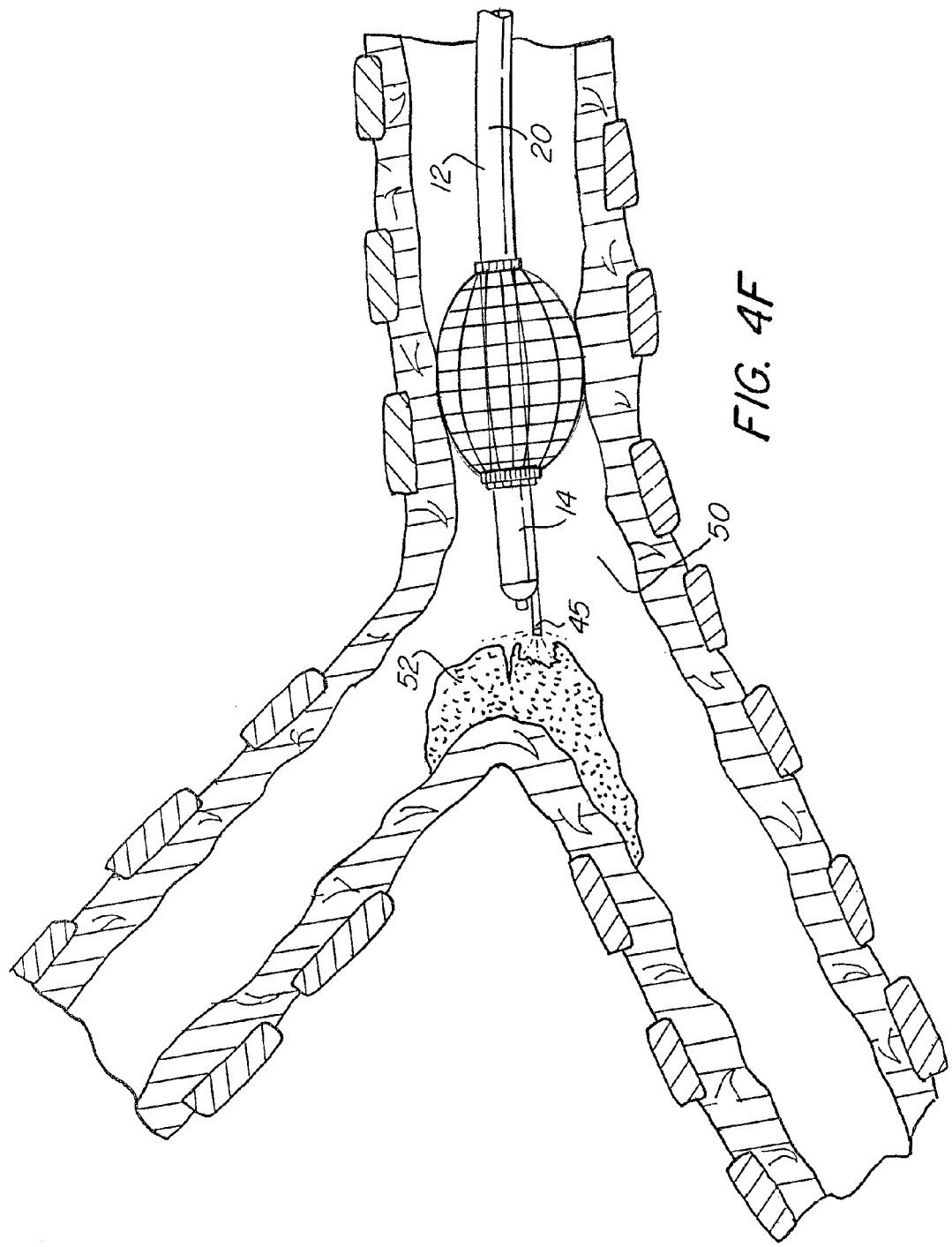

As shown in FIG. 4E-F, the needle (40) and forceps (42) containing bodily samples are withdrawn proximally into the catheter body (20), and if desired, additional diagnostic devices are deployed. The needle (40) and forceps (42) may be withdrawn from the lumens (36, 37) so that the additional diagnostic devices deployed therein. Alternatively, the catheter (20) may include additional lumens for these devices. As illustrated in FIG. 4E, an oxygen sensing probe (43) may be advanced into the tumor (52) to determine the partial pressure of oxygen therein. As illustrated in FIG. 4F, an optical fiber (45) or other appropriate device for performing optical sectioning is advanced out of the catheter (20) and acquires images with depth selectivity, from which three-dimensional representations of the biological material can be constructed. The balloon (16) may be inflated during this step in order to stabilize the catheter (20) within the biological cavity to ensure good image acquisition.

Figure 4H:
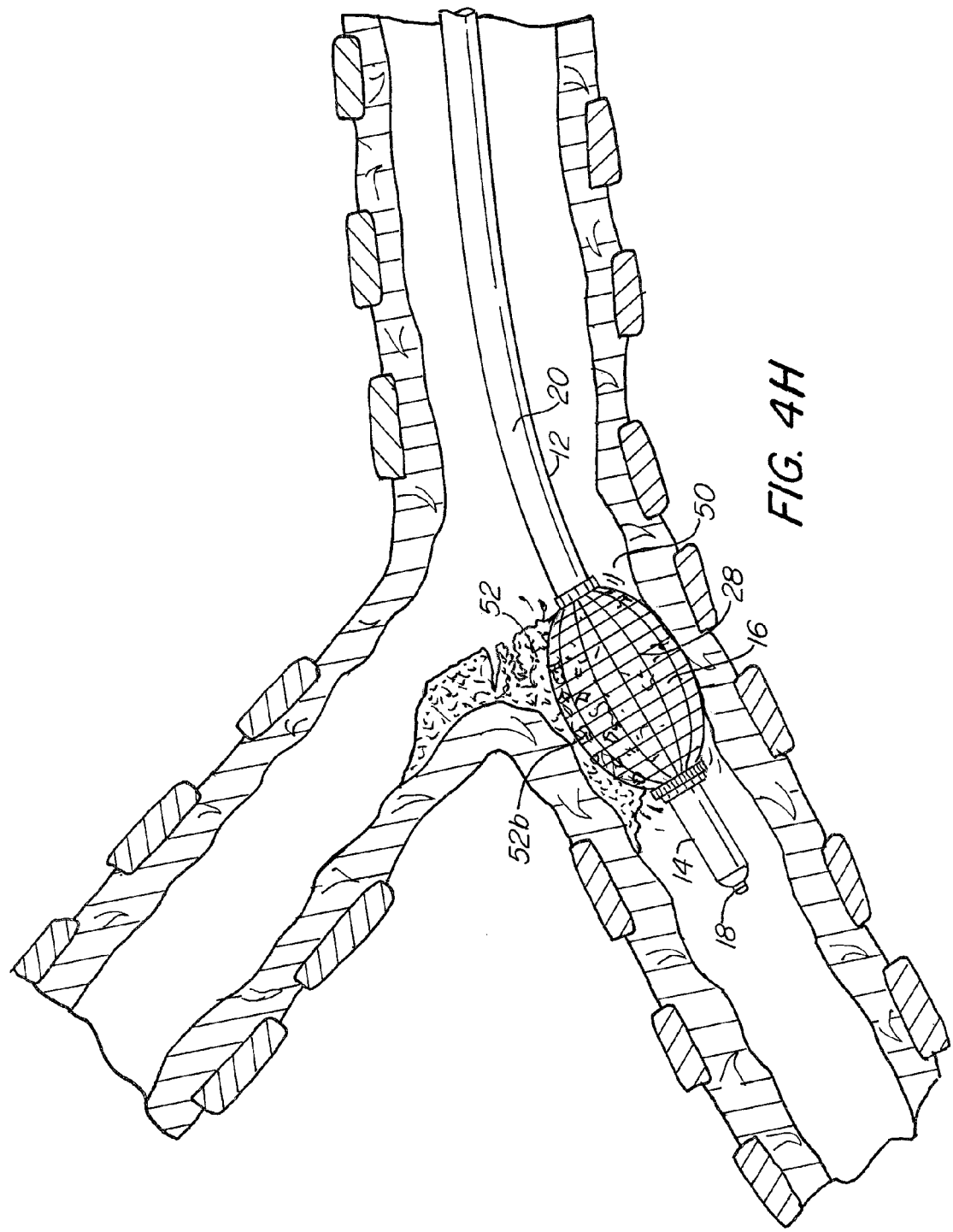

As shown in FIG. 4G-H, the balloon (16) is moved alongside the lumen wall and/or tumor (52). Depending on the particular procedure and/or vessel, the balloon may be moved while in an inflated state, such that it rubs along the tumor (52), or it may be deflated, moved alongside the tumor (52), and then inflated again. As the balloon (16) inflates and/or brushes along the surface of the lumen wall and/or tumor (52), the textured surface (28) abrades the wall of the lumen and/or tumor (52) and collects a cytological sample (52b). At this point, the catheter (20) may be rotated by manual means or via the control device to better position the device relative to the tissue site and allow the textured surface (28) of the balloon (16) to brush to the tissue (52) and cavity wall to collect a cytological sample (52b).

Figure 4I:
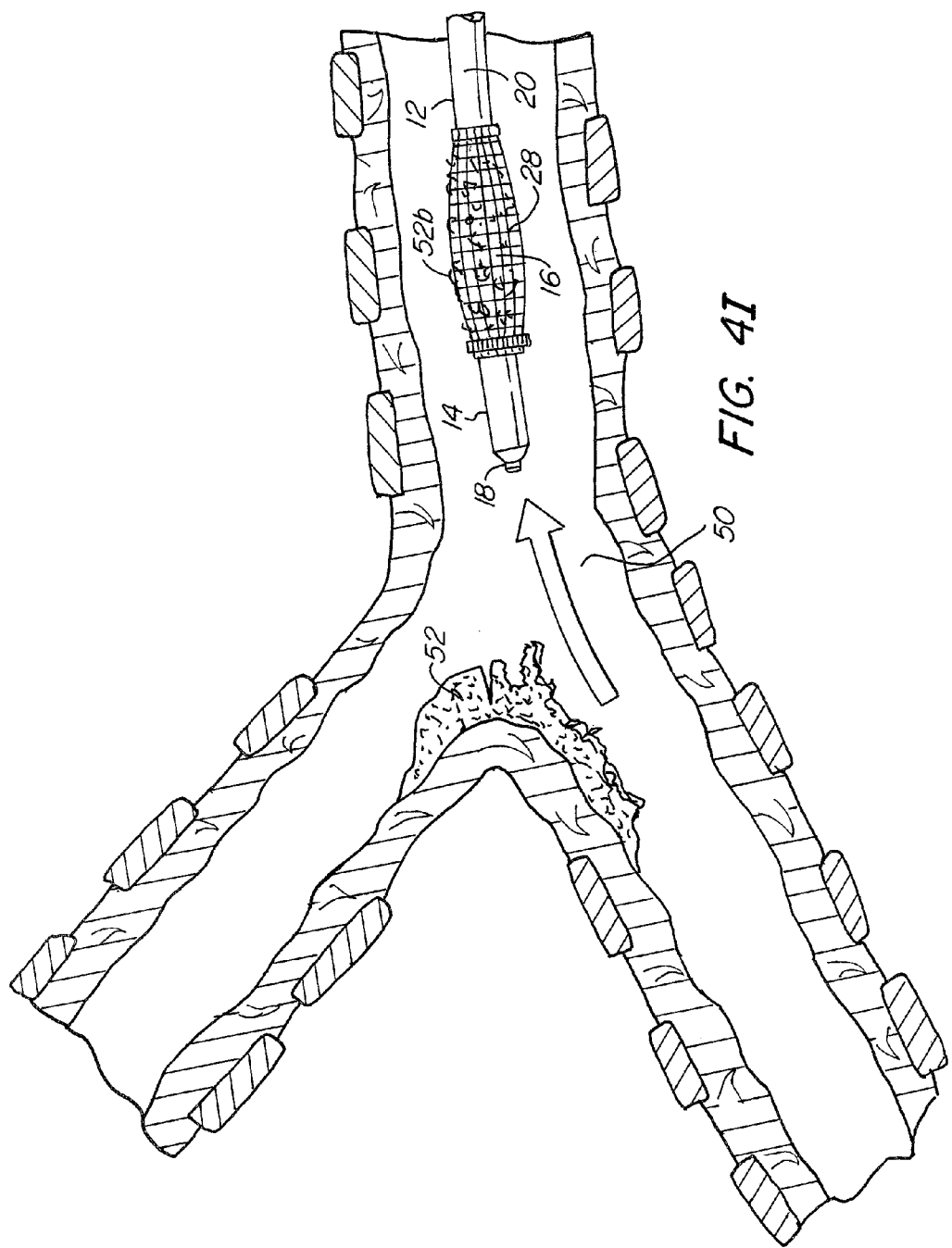

After the desired procedure is carried out completely, the balloon (16) is deflated, and the needle member (40) and forceps (42) are moved distally into the catheter body (20), as shown in FIG. 4I. Then, the system is safely withdrawn from the patient's body.

Figure 5A:
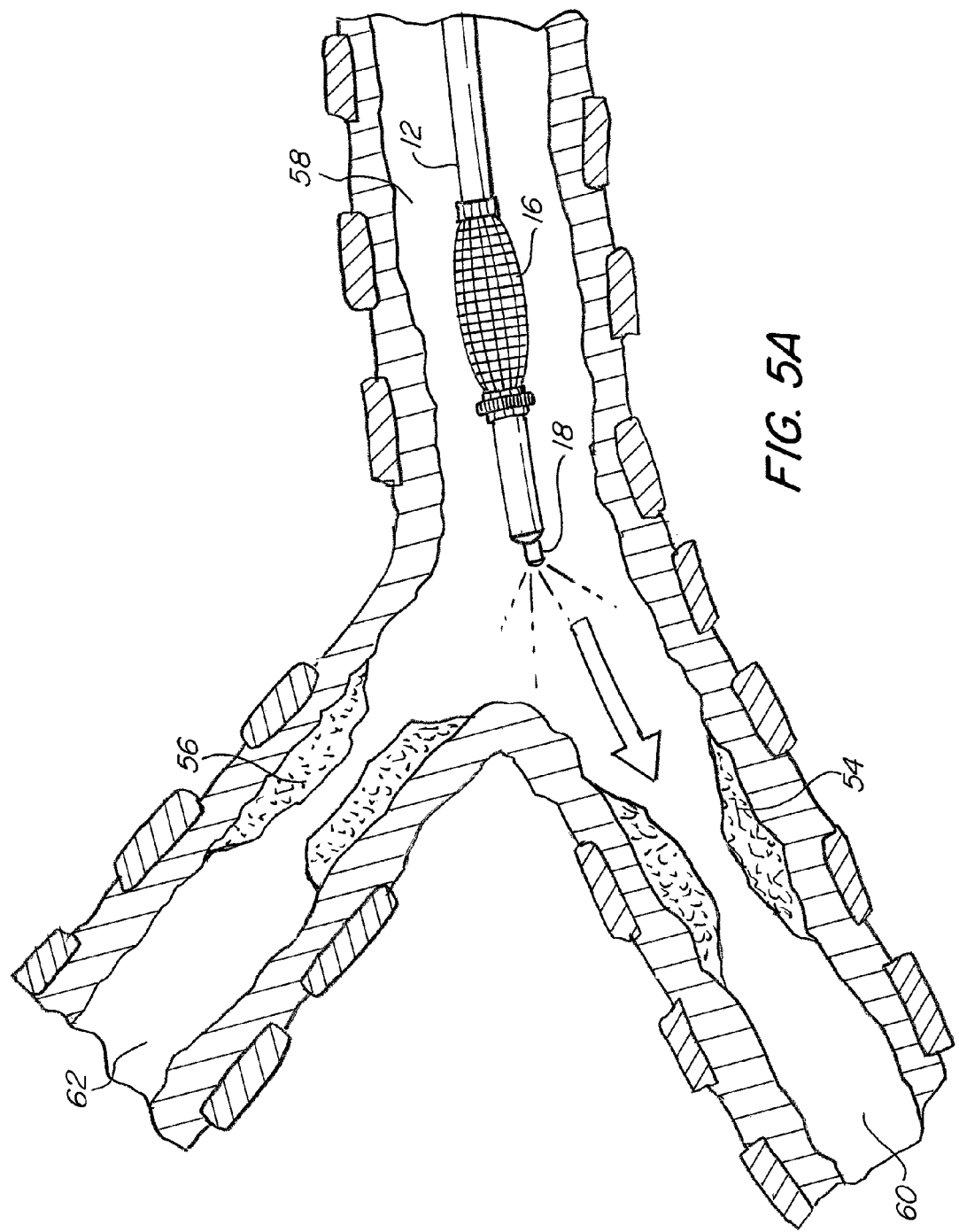
FIGS. 5A-5E are side elevation views of a balloon catheter system of the present invention deployed in a bronchus of the lung.

In another advantageous embodiment, shown in FIGS. 5A-5E, the balloon catheter (12) of the system (10) is inserted into a bronchus of the lung (58) with the balloon (16) in a deflated state. The balloon catheter (12) may contain one or more sample collection devices, such as needle (40) or forceps (42), disposed in a lumen thereof. Imaging device (18) is used to locate a bronchial junction containing target biological samples, such as tumors (54, 56), within bronchi or bronchioles on either side of the bronchial junction, as shown in FIG. 5A.

Figure 5B:
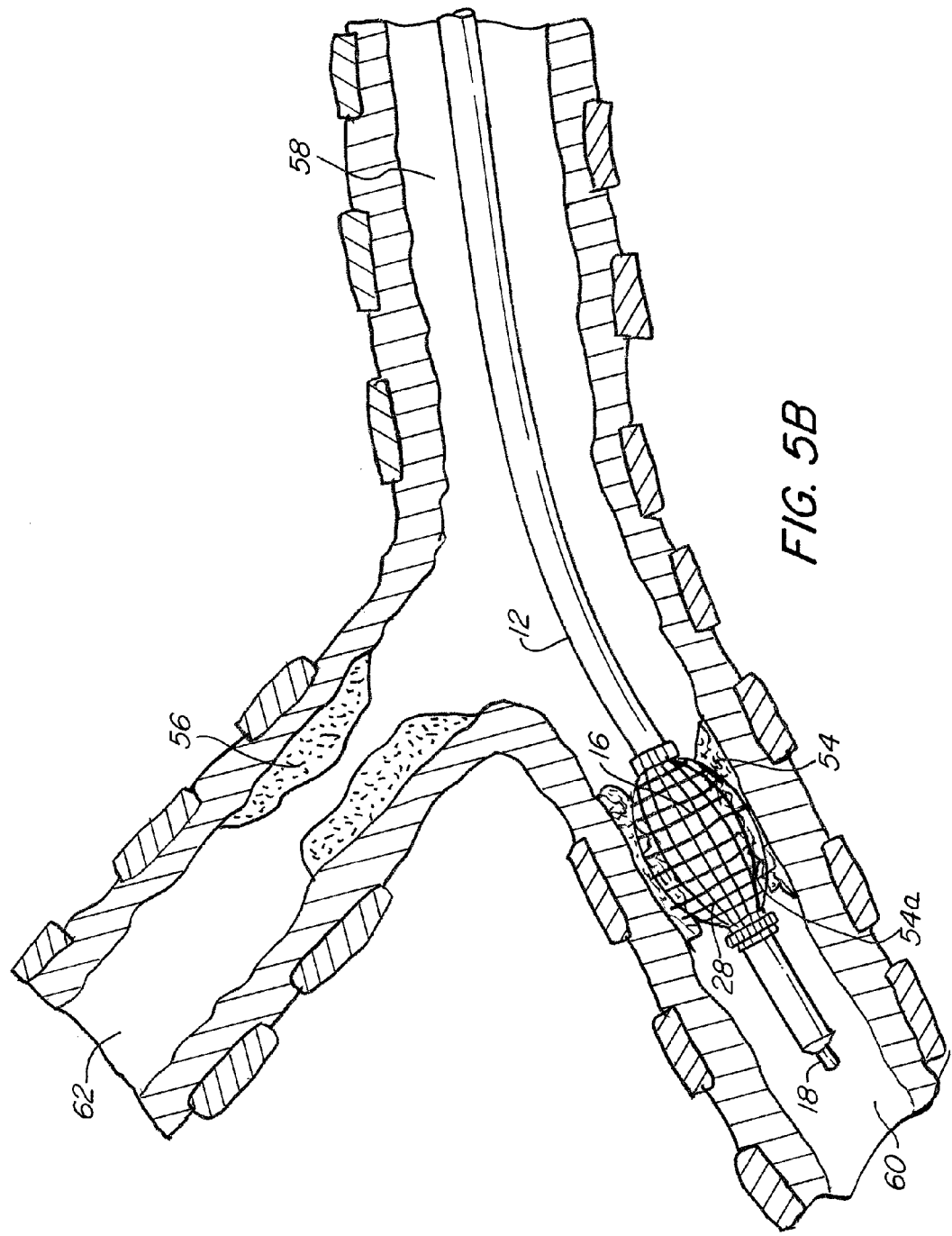

As shown in FIG. 5B, the catheter (12) is moved down a first bronchi (60) until the balloon (16) is adjacent to a first tumor (54). The balloon is inflated to collect a cytological sample (54a) via the textured outer surface (28). The balloon may be rotated by manual means or via a control device as previously discussed. A needle (40) and/or forceps (42) may be deployed out of the distal tip (14) to collect samples from the tumor in the manner previously discussed.

Figure 5C:
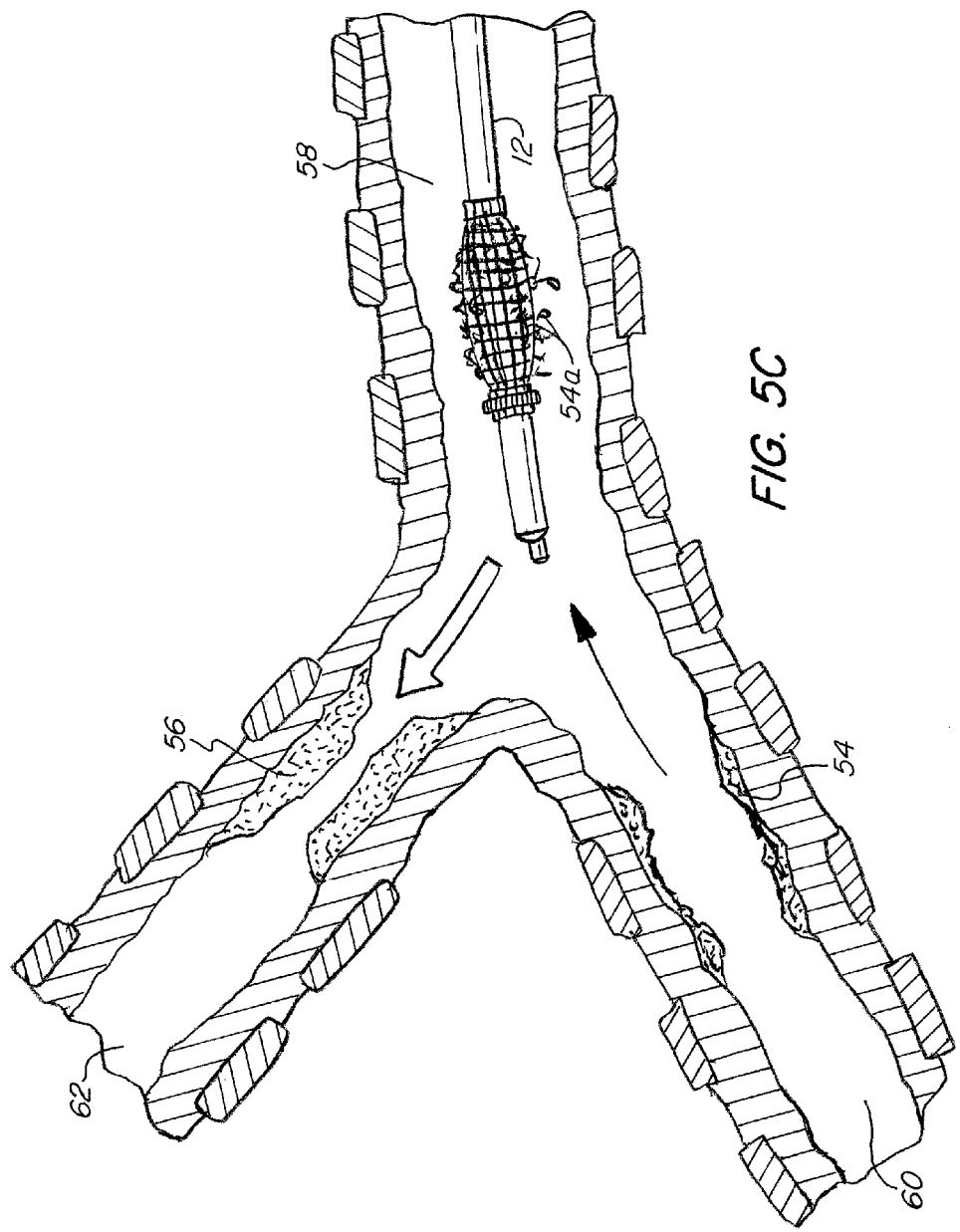
Figure 5D:
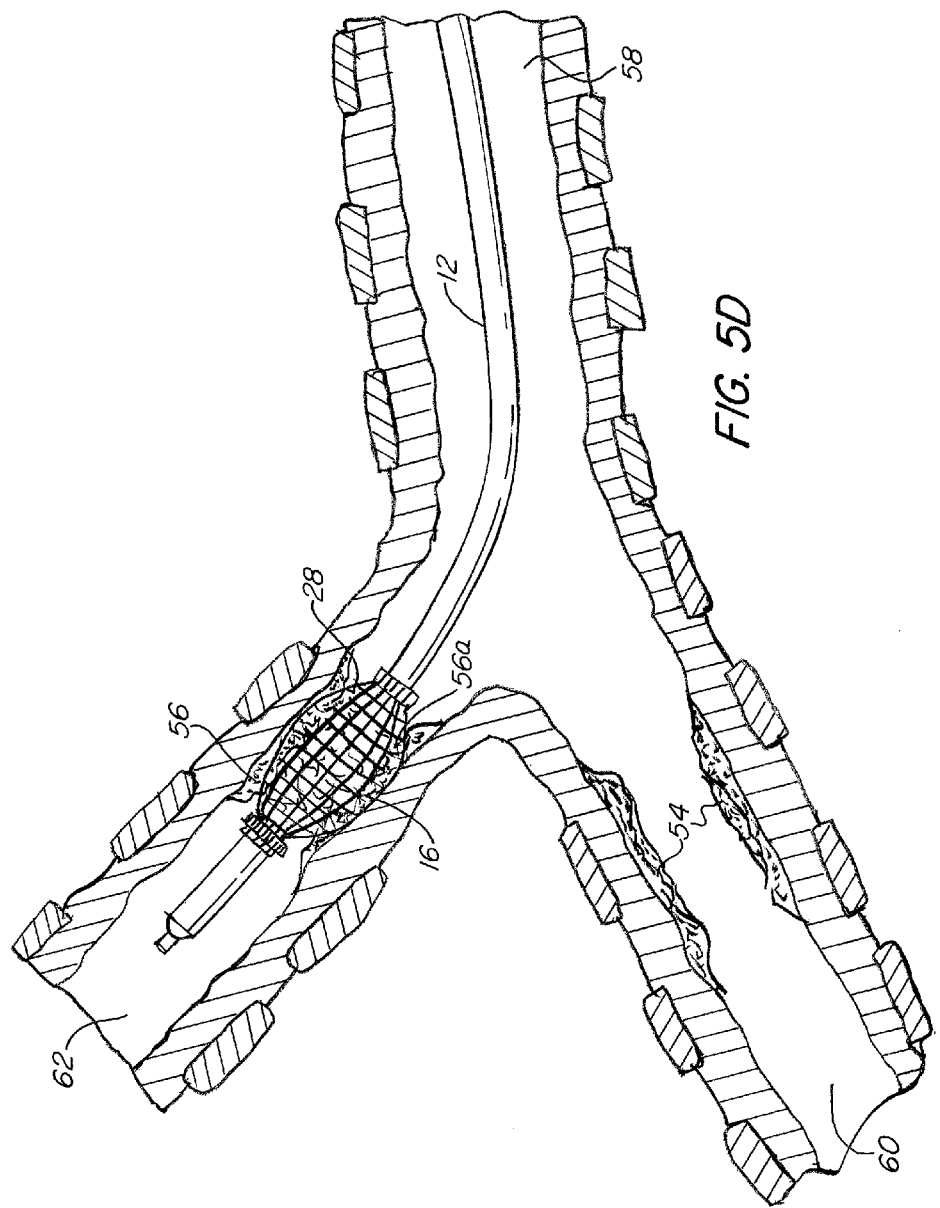

Following, the balloon (16) is slightly deflated and the catheter (12) is then removed from the first bronchi (60). As shown in FIG. 5C, the imaging device (18) is then used to guide the catheter into the second bronchi (62) of the bronchial junction. As shown in FIG. 5D, when the balloon is adjacent to the tissue or tumor (56) within the second bronchi (62), it is again inflated to collect a cytological sample (56a) via the textured outer surface (28). As with the first bronchi, the balloon may be rotated and/or a needle and forceps may be deployed to collect samples in the manner discussed.

Figure 5E:
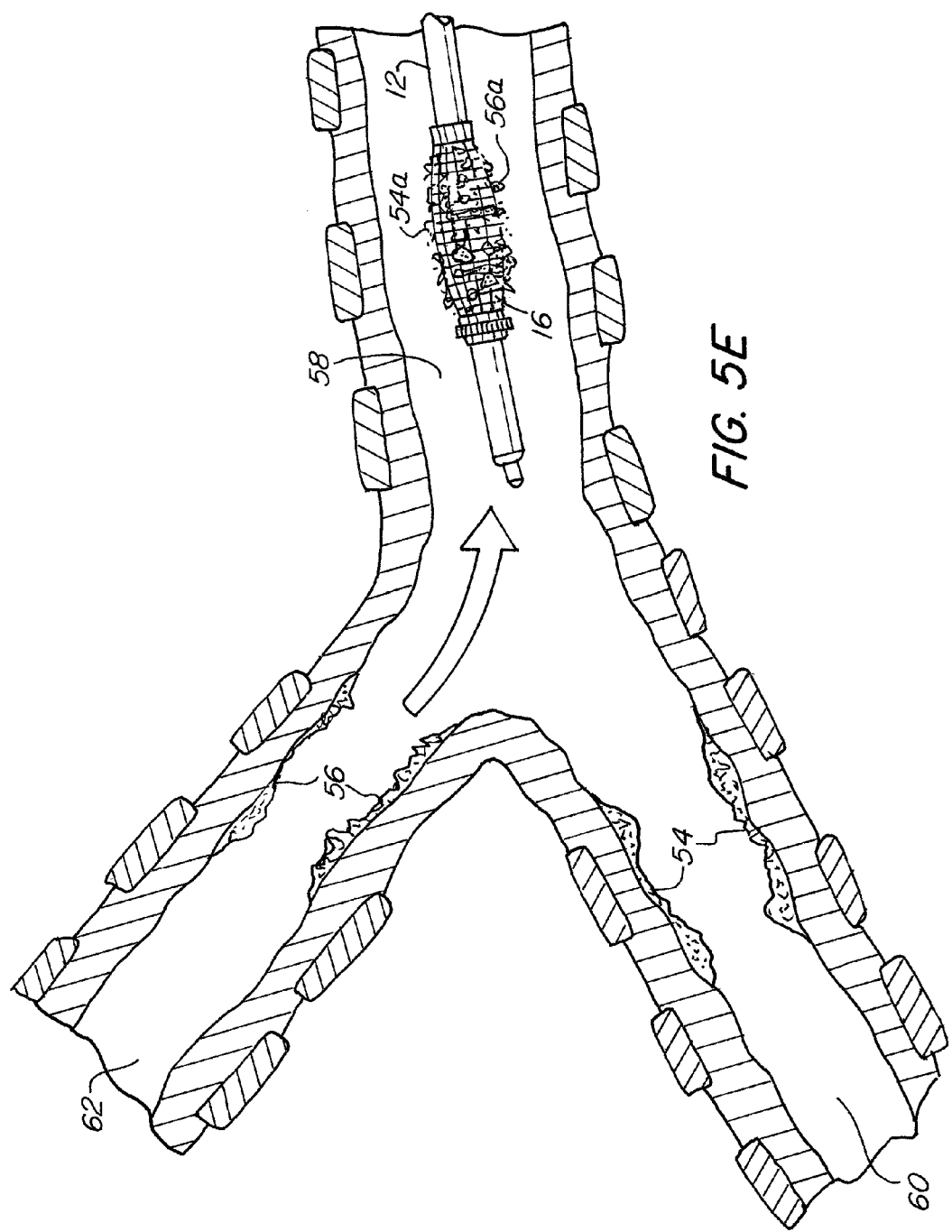

As shown in FIG. 5E, after the desired procedure is carried out completely, the balloon (16) containing the cytological samples (54a, 56a) is deflated, and the system is safely withdrawn from the patient's body.

It should be noted that, while the described embodiments have at times been described with respect to the lungs, the system may also be employed in other applications.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A system for gathering biological material in a biological cavity, comprising:
  a catheter having a first lumen, a balloon, and a second lumen in fluid communication with said balloon, said balloon having a textured outer surface for collecting biological material;
  at least one device for sampling biological material movably disposed in said first lumen; and
  a fluid source in fluid communication with said balloon that supplies fluid to said second lumen to inflate said balloon such that said textured outer surface collects additional biological material.

2. The system of claim 1, wherein said at least one device for sampling biological material comprises a forceps.

3. The system of claim 1, wherein said at least one device for sampling biological material comprises a needle.

4. The system of claim 3, wherein said catheter comprises a third lumen, further comprising a forceps movably disposed in said third lumen.

5. The system of claim 3, wherein said needle comprises a lumen fluidly connected to an opening at a distal end of the needle, further comprising a vacuum source for vacuuming material through the lumen of said needle.

6. The system of claim 1, further comprising an optical fiber for acquiring a diagnostic image of the biological material.

7. The system of claim 1, further comprising an oxygen sensing probe for determining the partial pressure of oxygen in the biological material.

8. The system of claim 1, further comprising at least one auxiliary lumen.

9. The system of claim 8, further comprising an imaging device disposed in one of said second lumen and said auxiliary lumen.

10. The system of claim 1, wherein the fluid source comprises an electro-pneumatic pump.

11. The system of claim 10, wherein the fluid is a gas.

12. The system of claim 1, wherein said textured surface is a mesh.

13. The system of claim 12, wherein said mesh comprises elastane.

14. The system of claim 1, wherein said catheter includes an imaging device aperture, and further comprising a fiber optic bundle disposed in said catheter and movable through said aperture for viewing said biological cavity.

15. The system of claim 1, wherein said catheter comprises an imaging marker.

16. The system of claim 1, wherein said balloon has first and second ends further comprising at least one imaging marker mounted adjacent at least one of said first end and second end of said balloon.

17. A method for gathering biological samples in a biological cavity, the method comprising the steps of:
inserting into a biological cavity a catheter having a first lumen, a balloon, and a second lumen in fluid communication with said balloon, said balloon having a textured outer surface for collecting biological material;
inserting a device for sampling biological material into and through the first lumen of said catheter;
collecting biological material with said device for sampling; and
supplying fluid through said second lumen to inflate said balloon such that the said textured outer surface comes into contact with and collects additional biological material.

18. The method of claim 17, wherein said device for sampling biological material comprises a needle, the step of collecting biological material with said device comprising puncturing a biological target with said needle.

19. The method of claim 17, wherein said at least one device for sampling comprises forceps, and the step of collecting biological material comprises severing a portion of a biological target.

20. The method of claim 19, wherein said at least one device for sampling comprises a needle, the step of collecting biological material further comprising puncturing said biological target with said needle.

21. The method of claim 17, wherein the step of inserting said device into and through the said first lumen comprises extending said device through the distal tip of said catheter.

22. The method of claim 17, further comprising the step of extending an imaging device through an additional lumen of said catheter and through said distal tip.

23. The method of claim 17, further comprising the steps of:
inflating said balloon to stabilize said catheter within the biological cavity; and
inserting an optical fiber through an additional lumen of the catheter to obtain a diagnostic image of the biological material.

24. The method of claim 17, further comprising the step of inserting an oxygen sensing probe through an additional lumen of the catheter to determine the partial pressure of oxygen in the biological material.

25. The method of claim 17, wherein the step of inserting a catheter comprises inserting a catheter into a bronchial airway.

26. The method of claim 25, further comprising the step of sweeping said inflated balloon along the bronchial airway.

27. The method of claim 17, wherein the step of inserting a catheter comprises inserting a catheter into a lung.

28. The method of claim 17, further comprising the step of evacuating biological samples through a lumen of said catheter using a vacuum source.

* * * * *